US009624550B2

(12) United States Patent
Yamauchi

(10) Patent No.: US 9,624,550 B2
(45) Date of Patent: Apr. 18, 2017

(54) METHODS FOR IDENTIFYING THE HABITATS OF INSECTS

(75) Inventor: Hiromasa Yamauchi, Kawasaki (JP)

(73) Assignee: SUNTORY HOLDINGS LIMITED, Osaka-shi, Osaka (JP)

( * ) Notice: Subject to any disclaimer, the term of this patent is extended or adjusted under 35 U.S.C. 154(b) by 1375 days.

(21) Appl. No.: 13/120,582

(22) PCT Filed: Sep. 17, 2009

(86) PCT No.: PCT/JP2009/066253
§ 371 (c)(1),
(2), (4) Date: Mar. 23, 2011

(87) PCT Pub. No.: WO2010/035686
PCT Pub. Date: Apr. 1, 2010

(65) Prior Publication Data
US 2011/0229901 A1    Sep. 22, 2011

(30) Foreign Application Priority Data

Sep. 26, 2008    (JP) .................................. 2008-249148

(51) Int. Cl.
*C12Q 1/68*        (2006.01)
*G06F 19/00*       (2011.01)

(52) U.S. Cl.
CPC ......... *C12Q 1/6888* (2013.01); *C12Q 1/6876* (2013.01); *C12Q 2600/156* (2013.01); *C12Q 2600/172* (2013.01)

(58) Field of Classification Search
None
See application file for complete search history.

(56) References Cited

FOREIGN PATENT DOCUMENTS

| JP | 2008-099644 | 5/2008 |
|---|---|---|
| JP | 2008-099644 A | 5/2008 |

OTHER PUBLICATIONS

Schlipalius et al. Genetic linkage analysis of the lesser grain borer Rhyzopertha dominica identifies two loci that confer high-level resistance to the fumigant phosphine. Genetics (2002) vol. 161, pp. 773-782.*
International Search Report dated Nov. 24, 2009 of PCT/JP2009/066253, filed Sep. 17, 2009.
Fleurat-Lessard, F. et al., "Genetic differentiation at the inter- and intra-specific level of stored grain insects using a simple molecular approach (RAPD)", Proceedings of the International Working Conference on Stored Product Protection, 2006, vol. 9th, pp. 446-455.
Zhang, L.P. et al., "Analysis of genetic diversity among different geographical populations and determination of biotypes of *Bemisia tabaci* in China", Journal of Applied Entomology, vol. 129, No. 3, 2005, pp. 121-128.
Su, Z.H. et al., "Origin and diversification of hindwingless *Damaster* ground beetles within the Japanese islands as deduced from mitochondrial ND5 gene sequences (Coleoptera, Carabidae)", Mol. Biol. Evol., 1998, vol. 15, No. 8, pp. 1026-1039.
Friedrich, M. et al., "Sequence and phylogenetic analysis of the completemitochondrial genome of the flour beetle *Tribolium castanaeum*", Mol. Phylogenet. Evol., 2003, vol. 26, No. 3, pp. 502-512.
Hiromasa Yamauchi et al., "DNA Tagata Kaiseki ni yoru Tribolium castanaeum no Yurai Chiiki no Tokutei", Japanese Journal of Forensic Science and Technology, Oct. 2008, vol. 13, p. 27.
Hiromasa Yamauchi et al., "DNA Kaiseki ni yoru Chokoku Gaichu Tribolium castanaeum no Seisoku Chiiki no Suitei", Japanese Society of Food Chemistry Dai 15 Kai Sokal.gakujutsu Taikai Koen Yoshishu, May 2009, vol. 15, p. 27.
Supplementary European Search Report mailed Jun. 13, 2012 in EP Application No. 09816101.1.
Braet, et al., DNA polymorphism detection in *Tribolium castaneum* (HERBST) (Coleoptera:Tenebrionidae): potential use in stored product pest management, DNA Sequence—The Journal of Sequence and Mapping. 1995, vol. 6, pp. 27-31.
Meštrović, et al., "Preliminary phylogeny of *Tribolium* beetles (Coleoptera: Tenebrionidae) resolved by combined analysis of mitochondrial genes", Éur. J. Entomol., vol. 103, No. 3, Jul. 2006, pp. 709-715.
Pai et al., "Identification of microsatellite markers in the red flour beetle, *Tribolium castaneum*", Molecular Ecology Notes, Sep. 2003, vol. 3, No. 3, pp. 425-427.
Zhong, et al., "AFLP-Based Genetic Linkage Map for the Red Flour Beetle (*Tribolium castaneum*)", Journal of Heredity, Jan. 2004, vol. 95, No. 1, pp. 53-61.
Angelini, et al., "Relationships among pest flour beetles of the genus *Tribolium* (Tenebrionidae) inferred from multiple molecular markers", Molecular Phylogenetics and Evolution, vol. 46, No. 1, Dec. 19, 2007, pp. 127-141.
Demuth et al., "Population Differentiation in the Beetle *Tribolium castaneum*. 1. Genetic Architecture", Evolution, vol. 61, No. 3, Mar. 2007, pp. 494-509.
Black et al., "Affordable assays for genotyping single nucleotide polymorphisms in insects", Insect Molecular Biology, vol. 16, No. 4, Aug. 2007, pp. 377-387.

(Continued)

*Primary Examiner* — David Thomas
(74) *Attorney, Agent, or Firm* — Drinker Biddle & Reath LLP

(57) ABSTRACT

A method for preparing a criterion for identifying the habitat of insects of the same kind, comprising the steps of:
(a) determining the nucleotide sequences of DNA of one or more insects from two or more habitats;
(b) aligning the nucleotide sequences determined in said step (a);
(c) eliminating sites consisting of one or more nucleotides conserved in all of the nucleotide sequences aligned in said step (b) from the nucleotide sequences;
(d) defining all or a part of the sites remaining upon elimination in said step (c) as type-discriminating sites;
(e) comparing nucleotides corresponding to each other in the type-discriminating sites obtained in said step (d) to classify completely identical type-discriminating sites as the same type and incompletely identical type-discriminating sites as one or more different types; and
(f) determining the habitat of each type classified in said step (e) on the basis of the habitats of insects belonging to each type, thereby defining the type-discriminating site of each type as a criterion.

2 Claims, 16 Drawing Sheets

(56) References Cited

OTHER PUBLICATIONS

Hirano et al., "A Trial to Analize Local Meta-Populations by the Use of the Snips of Mitochondrial ND5 Gene in Papilionid Butterfly *Luehdorfia japonica*," Behavior and Ecology, The Zoological Society of Japan, vol. 20, No. 12, p. 1618, 1.7-16, Dec. 25, 2003, Abstract Only.

Muraji et al., "Genetic variation of the green chafer, *Anomala albopilosa* (Hope) (Coleoptera: Scarabaeidae), in the Ryukyu Islands of Japan detected by mitochondrial DNA sequences," Applied Entomology and Zoology, vol. 43, No. 2, May 25, 2008, pp. 299-306.

Sha et al., "Mitochondrial phylogeography of a leafminer parasitoid, *Diglyphus isaea* (Hymenoptera: Eulophidae) in China," Science Direct, Biological Control, vol. 38, 2006, pp. 380-389.

* cited by examiner

Figure 24

$m^{th}$ criteria table (15 rows)　　　Sample nucleotide sequence list

| | Column 1 | Column 2 |
|---|---|---|
| Row 1 | A | 4 |
| Row 2 | G | 7 |
| Row 3 | A | 22 |
| Row 4 | C | 34 |
| Row 5 | G | 121 |
| ⋮ | ⋮ | ⋮ |
| Row r | T | i |
| ⋮ | ⋮ | ⋮ |
| Row 15 | C | 370 |

Corresponding (also identical in this example)

| | |
|---|---|
| G | No. 1 |
| C | No. 2 |
| A | No. 3 |
| A | No. 4 |
| T | No. 5 |
| ⋮ | |

PCR of method A
(amplified fragment
size 435 bp)

PCR of method B
(amplified fragment
size 179 bp)

1. Untreated
2. Boiled for 30 minutes
3. Boiled for 60 minutes
4. Autoclaved (121°C, 15 min)
5. Blank (without DNA)
M 100-bp DNA ladder 1 Sample 1
2 Sample 2
3 Blank (without DNA)
M 100-bp DNA Ladder 1 2K-1
2 2K-2
3 1.5K-1
4 1.5K-2
5 Blank (without DNA)
M 100 bp DNA Ladder

```
                          SEQUENCE LISTING

<160> NUMBER OF SEQ IDS NOS: 36

<210> SEQ ID NO 1
<211> LENGTH: 379
<212> TYPE: DNA
<213> ORGANISM: Tribolium castaneum

<400> SEQUENCE: 1
agaagtgtac attctaattc taccaggatt tggcataatc tcccacatta ttagacaaga     60
aagaggaaag aaagaagcat ttggaacact aggaataatt tatgcaataa tagcaattgg    120
gctcttaggt tttgttgtat gagcccatca catatttacc gtaggaatag acgttgatac    180
tcgagcctat ttcacttcag ccacaataat tattgctgtc ccaaccggga ttaaaatttt    240
tagatgacta gctactcttc acggcactca aattaattat agtccttcta taatatgggc    300
actaggattt gtattcctat ttacagtggg aggactaaca ggagtaatct tagcaaattc    360
atcaattgat attatactt                                                 379

<210> SEQ ID NO 2
<211> LENGTH: 379
<212> TYPE: DNA
<213> ORGANISM: Tribolium castaneum

<400> SEQUENCE: 2
agaggtatac attctaattc taccaggatt tggtataatc tcccacatta ttagacaaga     60
aagaggaaag aaagaagcat ttggaacact aggaataatt tatgcaataa tagcaattgg    120
gctcttaggt tttgttgtat gagcccatca catatttacc gtaggaatag acgttgatac    180
tcgagcctat ttcacttcag ccacaataat tattgctgtc ccaaccggaa ttaaaatttt    240
tagatgacta gccactcttc acggcactca aattaattat agtccttcta taatatgagc    300
```

```
actaggattt gtattcctat ttacagtggg gggactaaca ggagtaatct tagcaaattc    360
atcaattgat attatactt                                                 379
```

<210> SEQ ID NO 3
<211> LENGTH: 379
<212> TYPE: DNA
<213> ORGANISM: Tribolium castaneum

<400> SEQUENCE: 3

```
agaagtgtac attctaattc taccaggatt tggcataatc tcccacatta ttagacaaga     60
aagaggaaag aaagaagcat ttggaacact aggaataatt tatgcaataa tagcaattgg    120
gctcttaggt tttgttgtat gagcccacca catatttacc gtaggaatag acgttgatac    180
tcgagcctat ttcacttcag ccacaataat tattgctgtt ccaaccggaa ttaaaatttt    240
tagatgacta gccactcttc acggcactca aattaattat agcccttcta taatatgagc    300
actaggattt gtattcctat ttacagtggg aggactaaca ggagtaatct tagcaaattc    360
atcaattgac attatactt                                                 379
```

<210> SEQ ID NO 4
<211> LENGTH: 379
<212> TYPE: DNA
<213> ORGANISM: Tribolium castaneum

<400> SEQUENCE: 4

```
agaggtatac attctaattc taccaggatt tggtataatc tcccacatta ttagacaaga     60
aagaggaaag aaagaagcat ttggaacact aggaataatt tatgcaataa tagcaattgg    120
actcttaggt tttgttgtat gagcccatca catatttacc gtaggaatag acgttgatac    180
tcgagcctat ttcacttcag ccacaataat tattgctgtc ccaaccggaa ttaaaatttt    240
tagatgacta gccactcttc acggcactca aattaattat agtccttcta taatatgagc    300
actaggattt gtattcctat ttacagtggg gggactaaca ggagtaatct tagcaaattc    360
atcaattgat attatactt                                                 379
```

<210> SEQ ID NO 5
<211> LENGTH: 379
<212> TYPE: DNA
<213> ORGANISM: Tribolium castaneum

<400> SEQUENCE: 5

```
agaagtgtac attctaattc taccaggatt tggcataatc tcccacatta ttagacaaga     60
aagaggaaag aaagaagcat ttggaacact aggaataatt tatgcaataa tagcaattgg    120
gctcttaggt tttgttgtat gagcccacca catatttacc gtaggaatag acgttgatac    180
tcgagcctat ttcacttcag ccacaataat tattgctgtt ccaaccggaa ttaaaatttt    240
tagatgacta gccactcttc acggcactca aattaattat agcccttcta taatatgagc    300
actaggattt gtattcctat ttacagtggg aggactaaca ggagtaatct tagcaaattc    360
atcaattgac attatactt                                                 379
```

<210> SEQ ID NO 6
<211> LENGTH: 379
<212> TYPE: DNA
<213> ORGANISM: Tribolium castaneum

<400> SEQUENCE: 6

```
agaggtgtac attctaattc ttccaggatt tggtataatc tcccacatta ttagacaaga     60
```

```
aagaggaaag aaagaagcat ttggaacact aggaataatt tatgcaataa tagcaattgg    120
gctcttaggt tttgttgtat gggcccacca catatttacc gtaggaatag acgttgatac    180
tcgagcctat ttcacttcag ccacaataat tattgctgtt ccaaccggaa ttaaaatttt    240
tagatgacta gccactcttc acggcactca aattaattat agcccttcta taatatgagc    300
actaggattt gtattcctat ttacagtggg aggactaaca ggagtaatct tagcaaattc    360
atcaattgat attatactt                                                 379

<210> SEQ ID NO 7
<211> LENGTH: 379
<212> TYPE: DNA
<213> ORGANISM: Tribolium castaneum

<400> SEQUENCE: 7
agaggtgtac attctaattc ttccaggatt tggcataatc tcccacatta ttagacaaga     60
aagaggaaag aaagaagcat ttggaacact aggaataatt tatgcaataa tagcaattgg    120
gctcttaggt tttgttgtat gggcccacca catatttacc gtaggaatag acgttgatac    180
tcgagcctat ttcacttcag ccacaataat tattgctgtt ccaaccggaa ttaaaatttt    240
tagatgacta gccactcttc acggcactca aattaattat agcccttcta taatatgagc    300
actaggattt gtattcttat ttacagtggg aggactaaca ggagtaatct tagcaaattc    360
atcaattgat attatactt                                                 379

<210> SEQ ID NO 8
<211> LENGTH: 473
<212> TYPE: DNA
<213> ORGANISM: Tribolium castaneum

<400> SEQUENCE: 8
tataaaatct taagtaacct attcttataa tttcggcaac caaatccttt gaataaaatc     60
ctcttaaaaa tggtaatccg cacaaagata aatttctaat attaaaataa acacaagtta    120
aaggtaaaaa cttaactaag cccctatat  accgaatatc ctgaaaatca ccaactctat    180
gaataatatt cccagcacat ataaacaaca aagccttgaa taaagcatga gtcaataaat    240
ggaagaaagc tagttcatat cttcctaaag acaaaatcat tattattaaa ccaagctgtc    300
ttaaagtaga caaagcaata attttcttca aatcaaattc aaatctcgcc cctaacccgg    360
acataaacat tgtcattcta gaaataaata ataaaaaata tattaaccac tcattaaagc    420
aaaaattaaa acgaattaat aaatatacc   ctgccgttac taaagtagaa gaa          473

<210> SEQ ID NO 9
<211> LENGTH: 473
<212> TYPE: DNA
<213> ORGANISM: Tribolium castaneum

<400> SEQUENCE: 9
tataaaatct taagtaacct attcttataa tttcggcaac caaatccttt gaataaaatc     60
ctcttaaaaa tggtaatccg cacaaagata aatttctaat attaaaataa acacaagtta    120
aaggtaaaaa cttaactaag cccctatat  accgaatatc ctgaaaatca ccaactctat    180
gaataatatt cccagcacat ataaacaaca aagccttgaa taaagcatga gtcaataaat    240
ggaagaaggc tagttcatat cttcctaaag acaaaatcat tattattaaa ccaagctgtc    300
ttaaagtaga caaagcaata attttcttca aatcaaattc aaatctcgcc cctaacccgg    360
```

```
acataaacat tgtcattcta gaaataaata ataaaaaata tattaaccac tcattaaagc    420
aaaaattaaa acgaattaat aaatataccc ctgccgttac taaagtagaa gaa           473
```

<210> SEQ ID NO 10
<211> LENGTH: 473
<212> TYPE: DNA
<213> ORGANISM: Tribolium castaneum

<400> SEQUENCE: 10

```
tataaaatct taagtaacct attcttataa tttcggcaac caaatccttt gaataaaatc    60
ctcttaaaaa tggtaatccg cacaaagata aatttctaat attaaaataa acacaagtta   120
aaggtaaaaa cttaactaag cccctatat accgaatatc ctgaaaatca ccaactctat    180
gaataatatt cccagcacat ataaacaaca aagccttgaa taaagcatga gtcaataaat   240
ggaagaaggc tagttcatat cttcctaaag acaaaatcat tattattaaa ccaagctgtc   300
ttaaagtcga caaagcaata attttcttca aatcaaattc aaatctcgcc cctaacccag   360
acataaacat tgtcattcta gaaataaata ataaaaaata tattaaccac tcattaaaac   420
aaaaattaaa acgaattaat aaatataccc ctgccgttac taaagtagaa gaa           473
```

<210> SEQ ID NO 11
<211> LENGTH: 473
<212> TYPE: DNA
<213> ORGANISM: Tribolium castaneum

<400> SEQUENCE: 11

```
tataaaatct taagtaacct attcttataa tttcggcaac caaatccttt gaataaaatc    60
ctcttaaaaa tggtaatccg cacaaagata aatttctaat attaaaataa acacaagtta   120
aaggtaaaaa cttaactaag cccctatat accgaatatc ctgaaaatca ccaactctat    180
gaataatatt cccagcacat ataaacaaca aagccttgaa taaagcatga gtcaataaat   240
ggaagaaggc tagttcatat cttcctaaag acaaaatcat tattattaaa ccaagctgtc   300
ttaaagtcga caaagcaata attttcttca aatcaaattc aaatctcgcc cctaacccgg   360
acataaacat tgtcattcta gaaataaata ataaaaaata tattaaccac tcattaaagc   420
aaaaattaaa acgaattaat aaatataccc ctgccgttac taaagtagaa gaa           473
```

<210> SEQ ID NO 12
<211> LENGTH: 473
<212> TYPE: DNA
<213> ORGANISM: Tribolium castaneum

<400> SEQUENCE: 12

```
tataaaatct taagtaacct attcttataa tttcggcaac caaatccttt gaataaaatc    60
ctcttaaaaa tggtaatccg cacaaagata aatttctaat attaaaataa acacaagtta   120
aaggtaaaaa cttaactaag cccctatat accgaatatc ctgaaaatca ccaactctat    180
gaataatatt cccagcacac ataaacaaca aagccttgaa taaagcatga gtcaataaat   240
ggaagaaggc tagttcatat cttcctaaag acaaaatcat tattattaaa ccaagctgtc   300
ttaaagtcga caaagcaata attttcttca aatcaaattc aaatctcgcc cctaacccgg   360
acataaacat tgtcattcta gaaataaata ataaaaaata tattaaccac tcattaaagc   420
aaaaattaaa acgaattaat aaatataccc ctgccgttac taaagtagaa gaa           473
```

<210> SEQ ID NO 13
<211> LENGTH: 28

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(23)
<223> OTHER INFORMATION: a, c, t, g, unknown or other

<400> SEQUENCE: 13
ccggatcctt ytgrttytty ggncaycc                                           28

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 14
ccggatccac ancrtartan gtrtcrtg                                           28

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aaacagttaa amcartwgaa                                                    20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cctgtwtcwd ctttagtwca                                                    20

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aattattgct gtcccaaccg gg                                                 22

<210> SEQ ID NO 18
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 18
aattattgct gtcccaaccg ag                                              22

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggaatacaaa tcctagtgcc                                                 20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggaatacaaa tcctagtgac                                                 20

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aattattgct gtyccaaccg ga                                              22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aattattgct gtyccaaccg aa                                              22

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
rgaatacaaa tcctagtgct                                                 20

<210> SEQ ID NO 24
<211> LENGTH: 20
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 24
rgaatacaaa tcctagtgat                                                  20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gagtcaataa atggaagaaa                                                  20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gagtcaataa atggaagata                                                  20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gagtcaataa atggaagaag                                                  20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gagtcaataa atggaagatg                                                  20

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tttatgtccg ggttaggggc gag                                              23

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: Synthetic
```

```
                                     probe

<400> SEQUENCE: 30
caaccgggat taaaa                                                          15

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
caaccggaat taaaa                                                          15

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agcctatttc acttcagcca caat                                                24

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atgaatttgc taagattact cctgttagtc c                                        31

<210> SEQ ID NO 34
<211> LENGTH: 379
<212> TYPE: DNA
<213> ORGANISM: Rhyzopertha dominica

<400> SEQUENCE: 34
agaagtttac attttaatcc taccaggatt tggtataatt tctcatatta ttagacatga         60
aagaggaaaa aaggaaacct ttggttctct agggataatt tacgcaataa tagcaattgg        120
actattagga tttattgtat gagcacatca catatttact gtaggaatag acgtagatac        180
ccgagcatat tttacttcag caacaataat tattgcagtt ccaaccggaa ttaaagtatt        240
tagatgatta gctaccctcc acggaacaca aataaattat tcaccttcaa taatatgatc        300
attaggattt gtctttctat ttaccgtagg aggattaaca ggagtagtat tagcaaattc        360
atccattgat attattcta                                                    379

<210> SEQ ID NO 35
<211> LENGTH: 379
<212> TYPE: DNA
<213> ORGANISM: Rhyzopertha dominica

<400> SEQUENCE: 35
agaagtttac attttaatcc taccaggatt tggtataatt tctcatatta ttagacatga         60
aagaggaaaa aaggaaacct ttggttctct agggataatt tacgcaataa tagcaattgg        120
```
actattagga tttattgtat gagcacatca catatttacc gtaggaatag acgtagatac        180
ccgagcatat tttacttcag caacaataat tattgcagtt ccaaccggaa ttaaagtatt        240
tagatgatta gctaccctcc acggaacaca aataaattat tcaccttcaa taatatgatc        300
attaggattt gtctttctat ttaccgtagg aggattaaca ggagtagtat tagcaaattc        360
atccattgat attattcta                                                    379

<210> SEQ ID NO 36
<211> LENGTH: 379
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other
<220> FEATURE:
<221> NAME/KEY: modified_base
<222> LOCATION: (34)..(34)
<223> OTHER INFORMATION: a, c, t, g, unknown or other
<220> FEATURE:
<221> NAME/KEY: modified_base
<222> LOCATION: (121)..(121)
<223> OTHER INFORMATION: a, c, t, g, unknown or other
<220> FEATURE:
<221> NAME/KEY: modified_base
<222> LOCATION: (142)..(142)
<223> OTHER INFORMATION: a, c, t, g, unknown or other
<220> FEATURE:
<221> NAME/KEY: modified_base
<222> LOCATION: (148)..(148)
<223> OTHER INFORMATION: a, c, t, g, unknown or other
<220> FEATURE:
<221> NAME/KEY: modified_base
<222> LOCATION: (220)..(220)
<223> OTHER INFORMATION: a, c, t, g, unknown or other
<220> FEATURE:
<221> NAME/KEY: modified_base
<222> LOCATION: (283)..(283)
<223> OTHER INFORMATION: a, c, t, g, unknown or other
<220> FEATURE:
<221> NAME/KEY: modified_base
<222> LOCATION: (317)..(317)
<223> OTHER INFORMATION: a, c, t, g, unknown or other
<220> FEATURE:
<221> NAME/KEY: modified_base
<222> LOCATION: (331)..(331)
<223> OTHER INFORMATION: a, c, t, g, unknown or other
<220> FEATURE:
<221> NAME/KEY: modified_base
<222> LOCATION: (370)..(370)
<223> OTHER INFORMATION: a, c, t, g, unknown or other

<400> SEQUENCE: 36
agangtntac attctaattc tnccaggatt tggnataatc tcccacatta ttagacaaga        60
aagaggaaag aaagaagcat ttggaacact aggaataatt tatgcaataa tagcaattgg      120
nctcttaggt tttgttgtat gngcccanca catatttacc gtaggaatag acgttgatac      180

```
tcgagcctat ttcacttcag ccacaataat tattgctgtn ccaaccggra ttaaaatttt    240
tagatgacta gcyactcttc acggcactca aattaattat agnccttcta taatatgrgc    300
actaggattt gtattcntat ttacagtggg nggactaaca ggagtaatct tagcaaattc    360
atcaattgan attatactt                                                 379
```

METHODS FOR IDENTIFYING THE HABITATS OF INSECTS

CROSS REFERENCE TO RELATED APPLICATIONS

This application is the National Stage of International Application No. PCT/JP2009/066253, filed Sep. 17, 2009, and claims benefit of Japanese Application No. 2008-249148, filed Sep. 26, 2008, of which are herein incorporated by reference in their entirety.

INCORPORATION BY REFERENCE OF A SEQUENCE LISTING

A Sequence Listing is incorporated by reference that contains SEQ ID NOS: 1-35.

TECHNICAL FIELD

The present invention relates to methods for preparing a criterion for identifying the habitat of insects of the same kind by DNA analysis.

BACKGROUND ART

Japan is the world's largest importer of food. This food includes not only food products but also materials of food products such as soybean and feed grains such as corn. These are transported by air or sea from exporting countries to Japan and by land within the exporting countries.

Imported food may be verminated during storage in a domestic warehouse. This may be caused by contamination with insects inhabiting the warehouse or the exporting country or the transportation route, and it is very important to follow the route of contamination with the insects to take safety measures. However, some insects are distributed in various areas of the world, and in such cases where insects of the same morphology inhabit various areas, it was difficult to determine from their morphological features the place where the insects contaminated the food, i.e., the habitat of the insects, and it was also difficult to locate the cause of contamination with the insects.

DISCLOSURE OF THE INVENTION

Problems to be Solved by the Invention

The present invention provides methods for preparing a criterion for identifying the habitat of insects of the same kind by DNA analysis.

When food was contaminated with *Tribolium castaneum* during storage in a port warehouse, for example, as described above, there has been yet no means for identifying whether it was contaminated in the port warehouse with the insect inhabiting Japan or it was contaminated in the exporting country or on the transportation route with the insect inhabiting it, and it would be highly desirable to develop a technique for identifying the place where food was contaminated with pest insects.

Means for Solving the Problems

We devoted ourselves to our studies to solve the above problems. We analyzed the nucleotide sequences of the mitochondrial COI gene and ND5 gene of *Tribolium castaneum* from various areas in Japan and abroad to find that a habitat-specific polymorphism exists in each nucleotide sequence and achieved the present invention.

Accordingly, the present invention provides the following.

(1) A method for preparing a criterion for identifying the habitat of insects of the same kind, comprising the steps of:
(a) determining the nucleotide sequences of DNA of one or more insects from two or more habitats;
(b) aligning the nucleotide sequences determined in said step (a);
(c) eliminating sites consisting of one or more nucleotides conserved in all of the nucleotide sequences aligned in said step (b) from the nucleotide sequences;
(d) defining all or a part of the sites remaining upon elimination in said step (c) as type-discriminating sites;
(e) comparing nucleotides corresponding to each other in the type-discriminating sites obtained in said step (d) to classify completely identical type-discriminating sites as the same type and incompletely identical type-discriminating sites as one or more different types; and
(f) determining the habitat of each type classified in said step (e) on the basis of the habitats of insects belonging to each type, thereby defining the type-discriminating site of each type as a criterion.

(2) A method for preparing an area-discriminating criterion for identifying whether or not the habitat of insects of the same kind is an area, further comprising the following steps in addition to the steps as defined in (1):
(g) comparing nucleotides corresponding to each other in the criteria obtained in step (f) as defined in (1) to extract one or more nucleotides existing in only one type but not in the other types; and
(h) defining the one or more nucleotides extracted in said step (g) alone or in combination as an area-discriminating criterion.

(3) The method as defined in (1) or (2) wherein the insect is an insect belonging to the order Coleoptera.

(4) The method as defined in any one of (1)-(3) wherein the insect is an insect belonging to the family Tenebrionidae.

(5) The method as defined in any one of (1)-(4) wherein the insect is *Tribolium castaneum*.

(6) The method as defined in any one of (1)-(5) wherein the DNA is mitochondrial DNA.

(7) The method as defined in (6) wherein the mitochondrial DNA is the COI gene and/or ND5 gene.

(8) A method for identifying the habitat of a sample insect, comprising comparing the nucleotide sequence of an area having a criterion obtained by the method as defined in any one of (1)-(7) and a nucleotide sequence corresponding to the nucleotide sequence of an area having the criterion in a nucleotide sequence obtained from the sample insect, and analyzing whether or not a nucleotide at the site corresponding to the criterion in the nucleotide sequence of the sample is identical with the nucleotide of the criterion, thereby identifying the habitat of the sample.

(9) A method for identifying the habitat of a sample insect, comprising the steps of: storing a criteria table containing a data representing the nucleotide of a criterion obtained by the method as defined in any one of (1)-(7) and a data representing the location of the nucleotide in the nucleotide sequence into a computer on which a computer program for analysis runs, storing a sample nucleotide sequence list containing a data representing a nucleotide obtained from the sample insect, and allowing the computer to compare the data representing nucleotides at the corresponding locations in the nucleotide sequences between the sample nucleotide sequence list and the criteria table by referring to the data representing the location in the nucleotide sequence in the criteria table.

(10) The method as defined in (8) or (9) wherein the insect is an insect belonging to the order Coleoptera.

(11) The method as defined in any one of (8)-(10) wherein the insect is an insect belonging to the family Tenebrionidae.

(12) The method as defined in any one of (8)-(11) wherein the insect is *Tribolium castaneum*.

(13) The method as defined in any one of (8)-(12) wherein the DNA is mitochondrial DNA.

(14) The method as defined in (13) wherein the mitochondrial DNA is the COI gene and/or ND5 gene.

(15) A computer program for analysis for identifying the habitat of a sample insect, comprising a criteria table containing a data representing the nucleotide of a criterion obtained by the method as defined in any one of (1)-(7) and a data representing the location of the nucleotide in the nucleotide sequence.

(16) The computer program for analysis for identifying the habitat of a sample insect as defined in (15), which allows a computer to function as a means comprising a means for storing a sample nucleotide sequence list containing a data representing a nucleotide obtained from the sample insect and a means for comparing the data representing nucleotides at the corresponding locations in the nucleotide sequences between the sample nucleotide sequence list and the criteria table by referring to the data representing the location in the nucleotide sequence in the criteria table.

(17) A computer-readable medium on which the computer program for analysis as defined in (15) or (16) has been recorded.

(18) A criterion obtained by the method as defined in any one of (1)-(7).

(19) An area-discriminating criterion obtained by the method of (2) for identifying whether or not the habitat of *Tribolium castaneum* is the main island of Japan, wherein one or more of the following criteria are satisfied: the 229th nucleotide counted from the 5'-end of the nucleotide sequence derived from the *Tribolium castaneum* COI gene shown in SEQ ID NO: 1 is G, the 253rd nucleotide is T, and the 298th nucleotide is G, and/or the 248th nucleotide counted from the 5'-end of the nucleotide sequence derived from the *Tribolium castaneum* ND5 gene shown in SEQ ID NO: 8 is A.

(20) A primer comprising at least one of nucleotides constituting a criterion prepared by the method as defined in any one of (1)-(7).

(21) A probe comprising at least one of nucleotides constituting a criterion prepared by the method as defined in any one of (1)-(7).

(22) The primer as defined in (20) comprising a nucleic acid shown in SEQ ID NOs: 17-29 for identifying whether or not the habitat of *Tribolium castaneum* is the main island of Japan.

(23) A method for identifying the habitat of an insect using the primer as defined in (20) and/or the probe as defined in (21), comprising the steps of:
  (a) extracting DNA of a sample insect;
  (b) contacting the DNA extracted in said step (a) with the primer as defined in (20) and/or the probe as defined in (21);
  (c) amplifying a DNA fragment; and
  (d) identifying the habitat of the sample insect.

(24) A method for identifying the habitat of an insect using the primer as defined in (20) and the probe as defined in (21), comprising the steps of:
  (a) extracting DNA of a sample insect;
  (b) contacting the DNA extracted in said step (a) with the primer as defined in (20) and the probe as defined in (21);
  (c) amplifying a DNA fragment using real-time PCR;
  (d) detecting a fluorescent substance with which the probe has been labeled in advance; and
  (e) identifying the habitat of the sample insect.

(25) A method for identifying whether or not the habitat of *Tribolium castaneum* is the main island of Japan using the primer as defined in (22), comprising the steps of:
  (a) extracting DNA of a sample of *Tribolium castaneum*;
  (b) contacting the DNA extracted in said step (a) with the primer as defined in (22);
  (c) amplifying a DNA fragment; and
  (d) identifying whether the sample of *Tribolium castaneum* is *Tribolium castaneum* inhabiting the main island of Japan or *Tribolium castaneum* inhabiting another area.

(26) A method for identifying the habitat of an insect using the probe as defined in (21) and a pair of primers capable of amplifying the probe flanked therebetween, comprising the steps of:
  (a) extracting DNA of a sample insect;
  (b) contacting the DNA extracted in said step (a) with the probe as defined in (21) and a pair of primers capable of amplifying the probe flanked therebetween;
  (c) amplifying a DNA fragment using real-time PCR;
  (d) detecting a fluorescent substance with which the probe has been labeled in advance; and
  (e) identifying the habitat of the sample insect.

Advantages of the Invention

The ability to identify the habitat of *Tribolium castaneum* made it possible to clarify the cause of contamination of food with *Tribolium castaneum* by presuming the area where it was contaminated, and therefore, it can be expected that more effective safety measures could be rapidly taken.

Further, primers or probes for identifying the habitat can be prepared by using information of nucleotides constituting criteria prepared by the methods of the present invention. When DNA extracted from *Tribolium castaneum* of unknown habitat is used as a template and amplified by PCR using primers for the main island of Japan and primers for abroad areas of the present invention for identifying whether or not *Tribolium castaneum* inhabits the main island of Japan, for example, and if the primer for the main island of Japan is positive and the primer for abroad areas is negative, for example, it can be determined that the *Tribolium castaneum* is derived from the main island of Japan. Thus, the primers and probes are useful for simply identifying the habitats of insects.

In processed food or the like, DNA of contaminating insects is often fragmented. If DNA is fragmented, the region to be amplified by PCR may be segmented, which precludes amplification by PCR and DNA analysis so that the habitat of the contaminating insects cannot be determined. Thus, it is desirable that the fragment to be amplified by PCR corresponding to the DNA region to be analyzed should be short in advance. Advantageously, primers or the like of the present invention can be designed to cover PCR-amplified products as short as 1-200 base pairs (bp), preferably 1-100 base pairs (bp), more preferably 10-50 base pairs (bp) excluding the primer regions. Thus, such primers or the like of the present invention have the advantage that the influence of the DNA fragmentation can be as small as possible.

In the present invention, amplification by PCR was observed even if DNA of *Tribolium castaneum* was artificially degraded by heat or pressure treatment or DNA of *Tribolium castaneum* was artificially degraded by gamma irradiation, and its habitat could be identified by real-time PCR. Moreover, amplification by PCR was observed even in the case of *Tribolium castaneum* stored at room temperature for 5 months after having died of natural causes during raising. These results demonstrate a very wide range of applications of the present invention.

BRIEF DESCRIPTION OF THE DRAWINGS

FIG. 24 is a diagram showing a criteria table used with a computer program for analysis for identifying the habitat of an insect.

PREFERRED EMBODIMENTS OF THE INVENTION

Figure 1:
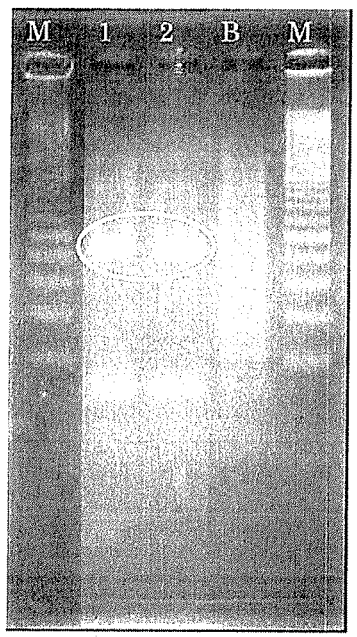
FIG. 1 is a photograph showing electrophoretic bands of DNA of the mitochondrial COI gene region of *Tribolium castaneum* from Thailand 1 and Okinawa 1.

The present invention will be specifically explained below, but should not be construed to be limited to the following description. The present invention relates to a method for preparing a criterion for identifying the habitat of insects of the same kind, the resulting criterion, a method for identifying the habitat of an insect using the criterion, a primer and a probe for identifying the habitat of the insect, and a computer program for analysis for identifying the habitat of the insect.

<Summary of the Present Invention>

The present invention is characterized by identifying the habitat of insects of the same kind by using a criterion. Specifically, DNA of a sample insect is extracted and the nucleotide sequence of a region corresponding to the nucleotide sequence of a criterion of the present invention is analyzed to evaluate whether or not the nucleotide sequence is identical with a nucleotide sequence corresponding to the criterion, and if it is identical, the habitat of the sample insect is identified as a habitat from the criterion.

<Insects of the Present Invention>

As used herein, "insects of the same kind" refer to insects showing no morphological difference typical of the habitat, and not only insects of the same species but any insect showing no morphological difference typical of the habitat can be used to prepare a criterion. In the current taxonomy, species are mainly classified by morphological differences, whereby insects belonging to the same species have the same morphology. In cases where insects having the same morphology are distributed in various areas of the world, it was difficult to identify the habitat of these insects from their morphological features. The present invention is characterized in that the habitats of insects that cannot be readily identified from their morphological features are rapidly and simply identified on the basis of molecular biology. As used herein, insects are those belonging to the subclass Pterygota making up a major part of the class Insecta in the phylum Arthropoda, preferably those belonging to the orders, but not limited to, Coleoptera, Diptera, Hymenoptera, Lepidoptera, Hemiptera, Orthoptera and Odonata. More specifically, they include, but not limited to, Order Coleoptera such as beetles; Order Diptera such as flies, mosquitoes and gadflies; Order Hymenoptera such as bees and ants; Order Lepidoptera such as butterflies and moths; Order Hemiptera such as cicadas and cabbage bugs; Order Orthoptera such as grasshoppers and crickets; Order Odonata such as dragonflies, etc., as described above.

*Tribolium castaneum* belonging to the family Tenebrionidae in the order Coleoptera is most widely known as an insect harmful to cereal powders such as flour and their secondary processed products such as cake and bread and often occurring in residences, food shops, flouring mills and feed mills, and it is distributed almost all over the world except for cold regions having an annual average temperature of 15° C. or less such as northern areas of the North American continent, Siberia and England. It is a preferable insect of the present invention because it shows no morphological difference typical of the habitat either in Japan or abroad.

The insects used for the preparation of a criterion of the present invention can be furnished or purchased from insect distributors or insect dealers, or can be collected in warehouses or factories, houses or in the field such as thickets or tussocks, or those found in food can also be used. The insects furnished or purchased or collected or otherwise obtained should be raised in isolation for each source to prevent insects of different sources from mixing.

<Habitat of an Insect of the Present Invention>

As used herein, the term "habitat of an insect" refers to the area where the insect lives. The area where an insect lives and country are not always identical, and insect diversity may occur in an area isolated by sea even in the same country or in an area isolated by river or mountain even in neighboring areas. On the other hand, the same insect in terms of molecular biology may grow across a plurality of different countries belonging to the same continent. Moreover, an insect derived from the area of shipment may inhabit an airport or harbor on the transportation route as a result of the development of worldwide transportation. After the cargo carrying the insect derived from the area of shipment is transported to a factory and unpacked, the insect may further inhabit a surrounding area of the factory. Therefore, the term "area" as used herein includes not only country-based areas but also continents, areas or regions in the same country, places through which cargo is transported such as airports and harbors, and warehouses and factories as described above.

<Criterion of the Present Invention>

As used herein, the term "criterion" refers to an indicator for identifying the habitat of an insect, and defines a habitat corresponding to each type classified on the basis of single nucleotide polymorphism, as explained in detail below. One or more habitats may correspond to one type. When an insect derived from the area of shipment inhabits a place on the transportation route, for example, the type-discriminating sites of insects inhabiting the area of shipment and the insect inhabiting the place on the transportation route are presumed to belong to the same type, whereby one type covers the two habits, i.e., the area of shipment and the place on the transportation route. As shown in the Examples below and Table 1, a plurality of types may exist in one area. Specifically, Table 1 shown below demonstrates that two haplotypes exist in each area except for the nucleotides from the main island of Japan. As used herein, haplotype means that a nucleotide sequence containing different polymorphisms, i.e., multiple single nucleotide polymorphisms (SNPs) on homologous DNA molecules of organisms of the same kind shows a pattern of a whole set of changes. For example, a haplotype relation exists between Okinawa 2-5 of Japan type 2 and Okinawa 1 of Japan type 3; Thailand 1, 3-5 of abroad type 1 and Thailand 2 of abroad type 2; Canada 1, 4, 5 of abroad type 3 and Canada 2, 3 of abroad type 4, in Table 1 shown below. In such cases, multiple types exist in one area.

The DNA nucleotide sequence (hereinafter sometimes referred to as "sequence data") of an insect used for preparing a criterion of the present invention may be derived from mitochondrial DNA or nuclear DNA. Especially, mitochondrial DNA is preferable because it is undergoes nucleotide substitutions more rapidly than nuclear DNA so that it is thought to be more variable between habitats and the greater number of copies per cell allows preparation in large amounts and therefore facilitates analysis.

Examples of criteria of the present invention include those as shown in Table 1. Table 1 shows the results of nucleotide analysis of single nucleotide polymorphisms in the two mitochondrial gene COI region and ND5 region of *Tribolium castaneum*, revealing 15 and 5 polymorphisms typical of their own habitat in the COI region and ND5 region, respectively, whereby the sequences are classified in seven types at the present. The criteria table can be used to analyze, for example, the COI region (379 bp in length) and ND5 region (473 bp in length) of mitochondrial DNA of a sample of *Tribolium castaneum* and determine the type to which it belongs, thereby identifying the habitat of the sample of *Tribolium castaneum*. Areas that can be currently determined include the main island of Japan, Okinawa, Thailand and Canada, but criteria can be increased and more areas can be determined by analyzing mitochondrial DNA of *Tribolium castaneum* derived from other habitats to evaluate polymorphisms.

<Method for Preparing a Criterion of the Present Invention>

The present invention relates to a method for preparing a criterion for identifying the habitat of insects of the same kind, specifically comprising the steps of:

(a) determining the nucleotide sequences of DNA of one or more insects from two or more areas;

(b) aligning the nucleotide sequences determined in said step (a);

(c) eliminating sites consisting of one or more nucleotides conserved in all of the nucleotide sequences aligned in said step (b) from the nucleotide sequences;

(d) defining all or a part of the sites remaining upon elimination in said step (c) as type-discriminating sites;

(e) comparing nucleotides corresponding to each other in the type-discriminating sites obtained in said step (d) to classify completely identical type-discriminating sites as the same type and incompletely identical type-discriminating sites as one or more different types; and (f) determining the habitat of each type classified in said step (e) on the basis of the habitats of insects belonging to each type, thereby defining the type-discriminating site of each type as a criterion.

However, the present invention is not limited to these methods, and appropriate modifications of other commonly known methods can be also used.

(a) Step of Determining the Nucleotide Sequences of DNA of One or More Insects from Two or More Habitats DNA of one or more insects from two or more habitats is used for preparing a criterion in the present invention.

As used herein, the term "DNA from two or more habitats" means that 2 or more, preferably 5 or more, more preferably 7 or more sequence data of insects having the same morphology but different habitats are used. The habitats of the insects used can be appropriately selected for the purpose of application of the criterion, but preferably should be selected from geographically isolated areas so that differences can be found between the habitats. The term "DNA of one or more insects" means that one or more, preferably 3 or more, more preferably 5 or more sequence data of insects from each habitat as described above are used. This allows for the preparation of a habitat-specific and reliable criterion.

Sequence data of an insect used for preparing a criterion of the present invention may be the routinely determined nucleotide sequence of DNA uniquely extracted from the insect. A method for uniquely extracting DNA from an insect to determine the nucleotide sequence is illustrated below.

(1) Collection of Insects

The "DNA" used in the present invention can be extracted from the whole body or a part (feeler, thorax, wing, leg, etc.) of an insect. It is preferable to use the whole body of one or a few individuals in the case of small insects such as Phoridae or a part of the body (any one of feeler, thorax (or the muscle thereof), fore wing, hind wing, leg, etc.) in the case of large insects such as *Musca domestica* or longer insects.

(2) Extraction of DNA

DNA can be extracted by using a method known in the art including the CTAB (Cetyltrimethyl ammonium bromide) method or using a commercially available kit such as Qiagen DNeasy Tissue Kit (Qiagen) or ISOPLANTII (NIPPON GENE CO., LTD.). In terms of runnability and economy, the CTAB method is preferable.

(3) Amplification of a DNA Fragment

The DNA extracted as above is amplified by a PCR method. The PCR method used in the present invention is not specifically limited, and includes known PCR methods and various improved methods. An example is shown below. That is, a primer set and the template DNA are mixed with reagents such as Tris-HCl, KCl, $MgCl_2$, each dNTP, TaqDNA polymerase to prepare a PCR solution. One cycle of PCR consists of three steps: thermal denaturation, annealing, and elongation (synthesis) reaction of a DNA chain with a DNA polymerase. Each step requires a different or the same reaction temperature and reaction period, which are appropriately determined depending on the nucleotide sequence, the length and others of a DNA region to be amplified. These procedures can be achieved by using a commercially available thermal cycler.

Examples of primers used in the present invention include existing primers used for phylogenetic analysis of insects as described in the Examples below, including a primer set derived from the mitochondrial cytochrome oxidase subunit I (COI) gene (L6625/H7005 (SEQ ID NOs: 13 and 14)) and/or a primer set derived from the NADH dehydrogenase subunit 5 (ND5) gene (F6999/R7495 (SEQ ID NOs: 15 and 16)).

In cases where a desired band cannot be amplified with existing primers in some insect species, suitable primers flanking the nucleotide of the criterion, i.e., a region containing the nucleotide of the criterion are designed and used. The primers are preferably selected to allow for the amplification of a desired band in more insect species.

(4) Verification of Amplification by PCR

As a method for evaluating the results of PCR (PCR products), any method allowing for the identification of a specific DNA fragment such as e.g., electrophoresis, gel filtration or hybridization is used to verify that a DNA fragment of a desired size has been amplified. For example, verification is made that a fragment of 435 bp in length has been amplified when a primer set derived from the mitochondrial COI gene is used, or that a fragment of 513 bp in length has been amplified when a primer set derived from the ND5 gene is used.

(5) Purification of the PCR Products

The amplified PCR products are separated from components used for the reaction such as excessive primers so that they may be used as templates for cycle sequencing reaction. This purification can be performed by using, e.g., a commercially available QIAquick PCR Purification Kit (Qiagen) following the attached protocol.

(6) Cycle Sequencing Reaction and Purification of the Sequenced Products

For sequencing the PCR products purified as described above, they are used as templates to perform a cycle sequencing reaction. This method is similar to PCR, and comprises repeating three steps of thermal denaturation, annealing, and elongation reaction of a DNA chain with a DNA polymerase using a thermal cycler to synthesize various single-stranded DNA fragments of different lengths using either one primer in the presence of a terminator labeled with four different fluorescent dyes each for one nucleotide. Cycle sequencing may be performed by using a commercially available BigDye Terminator v1.1 Cycle Sequencing Kit (ABI), for example. Specifically, the procedure can be performed following the Japanese protocol of the kit ("Cycle sequencing of single-stranded DNA and double-stranded DNA" at p. 22, "Cycle sequencing in GeneAmpPCR System 9700, 9600, 2700, 2400" at p. 25, and "Purification method on spin columns (or spin plates)" at pp. 38-40). The nucleotide sequences of the primers used may be the same as those used for the amplification of a desired DNA fragment by PCR. That is, predetermined materials are added to a purified solution of the PCR product optionally diluted with sterile distilled water to prepare a cycle sequencing reaction solution. A PCR microtube containing this solution is placed in a PCR reactor to perform denaturation (e.g., 96° C., 1 minute) followed by e.g., 25 cycles of denaturation (e.g., 96° C., 10 seconds), annealing (e.g., 50° C., 5 seconds) and elongation (e.g., 60° C., 4 minutes). When the sample cannot be collected immediately after completion of the reaction, the temperature of the sample block may be lowered and kept at that level.

Then, a mixed solution of the sequenced products, i.e., single-stranded DNA is purified from the reaction solution obtained above to prepare a sample for use in the subsequent sequencer. An example of this method is a method using CENTRISEP Spin Column (ABI) following the attached protocol to prepare a desired sample.

(7) Sequencing of DNA Fragments

The sequenced products obtained by the Dye Terminator method described above are sequenced. A typical method uses electrophoresis, and as an example, comprises performing electrophoresis using ABI PRISM 310 Genetic Analyzer, and sequentially determining the nucleotide sequences by a laser fluorescent detector on the basis of the difference of the fluorescent substances used as labels between the nucleotides.

(8) Analysis of the Nucleotide Sequences

The nucleotide sequences determined are analyzed to provide sequence data. When a primer set derived from the mitochondrial COI gene and ND5 gene is used for example, a sequence data of 300-600 bp in length is obtained from each of the 5'-end (on the side of primer L6625 or F6999) and the 3'-end (on the side of primer H7005 or R7495). The sequence data obtained were verified to determine exact nucleotide sequences.

The sequence data of an insect used as a criterion of the present invention may be the routinely determined nucleotide sequence of DNA uniquely extracted from the insect, or may be a known sequence data available from a public database. Known sequence data that can be used include e.g., sequence data of insects in databases such as databases of GeneBank (NIH genetic sequence database) and DDBJ (DNA Data Bank of Japan). The sequence data searched and downloaded from these databases can be used for alignment (multiple alignment analysis) directly or after a continuous region has been extracted. In this case, it is preferable that the habitat such as the place of collection of the insect from which the sequence data in the database is derived has been identified.

(b) Step of Aligning the Nucleotide Sequences

The sequence data of at least one individual insect per habitat is selected for two or more habitats from the results of actual analysis obtained as above or known data, and aligned as described above.

As used herein, alignment refers to a procedure in which a plurality of nucleotide sequences obtained from individuals are arranged in rows so that homologous residues appear in successive columns, thereby determining homology between the nucleotide sequences. Such a procedure is also referred to as multiple alignment and conventionally used in the field of molecular biology for the extraction of a motif in a certain nucleotide sequence, the presumption of the structure or function of a particular nucleotide sequence, and the preparation of an evolutionary genealogy. Thus, the alignment of the present invention includes any procedure normally used for these analyses such as the use of a computer program for analysis such as DNAspace (from Hitachi Software Engineering Co., Ltd.). Sequence data used for alignment in the present invention include nucleotide sequences of 20 bp or more, preferably 50 bp or more, more preferably 20-10000 bp, more preferably 50-5000 bp in length.

Sequence data from a plurality of insects used in the present invention must contain a shared region (hereinafter also referred to as "consensus region") so that they may be aligned. Thus, for example, a sequence data obtained by actual analysis, i.e., a region amplified with desired primers and sequenced is defined as a consensus region, and a sequence data containing the consensus region is selected from a public database and used directly or a continuous region has been extracted. More specifically, the name of the species or subspecies and the name of a protein (enzyme, etc.) encoded by the gene are used as keywords to search a database, or homology search (BLAST search) is performed on the basis of a sequence data obtained by actual analysis and a sequence data having the region of the sequence data obtained by actual analysis is selected and downloaded. The downloaded sequence data can be used for alignment (multiple alignment analysis) directly or after a continuous region has been extracted. The consensus region selected is not specifically limited, and may be a region expressing a specific function or structure such as the mitochondrial ND5 gene or a genetically unfunctional region. When a highly variable region between habitats is known in advance, such a region is preferably selected. For example, mitochondrial genomes are preferable because they have a greater number of copies without repair function and rapidly evolve so that they are thought to be more variable between habitats and they are known to more exactly reflect genealogical relationships because they are maternally inherited. Specifically, the mitochondrial COI gene and ND5 gene are especially preferable as consensus regions of criteria because they rapidly evolve and are thought to be more variable between habitats. The consensus region is preferably amplifiable by PCR. For example, such regions include regions amplifiable by using the primers described in the Examples below. The size of the consensus region is selected to provide reliable sequencing in the range of about 20-2000 bp, about 50-1000 bp, preferably, 100-700 bp, more preferably 100-500 bp.

The consensus region for preparing a criterion may not be one region, but multiple regions may be selected. A more habitat-specific criterion can be prepared by using multiple regions. Specifically, a criterion specific to the habitat of *Tribolium castaneum* can be prepared by analyzing the sequences in the COI gene region and the ND5 gene region of *Tribolium castaneum* by multiple alignment using a computer program for analysis such as ClustalW2 of EMBL-EBI on the internet and finding single nucleotide polymorphisms (SNPs) in each region, and then combining them, as described in the Examples below.

(c) Step of Eliminating Nucleotides Conserved in all of the all Nucleotide Sequences Above Then, sites consisting of one or more nucleotides conserved in all of the nucleotide sequences aligned in this manner are eliminated from the nucleotide sequences above. Such elimination of regions of nucleotides conserved in all of the nucleotide sequences clearly reveals the presence of single nucleotide polymorphisms and facilitates SNP-based typing in the subsequent.

Specifically, sites of nucleotides conserved in the nucleotide sequences of all of the individuals are extracted from the data obtained by alignment. The term "nucleotide conserved" means that all of the nucleotide is same in a column of the resulting alignment data in the nucleotide sequences of all of the individuals. All of the extracted sites are eliminated. The reason why all of the conserved sites are eliminated is explained below.

When the nucleotide sequences of insects of the same morphology are compared, almost nucleotides may be shared by all of the individuals. However, the present invention is characterized by focusing on single nucleotide polymorphisms rather than residues shared by all of the individuals and intended to prepare a criterion based on the finding of a correlation between the single nucleotide polymorphisms and habitats. Any method capable of extracting nucleotides conserved in the nucleotide sequences of all of the individuals can be used, such as visual or mechanical manipulation.

(d) Step of Preparing Type-Discriminating Sites

All or a part of the sites remaining upon elimination as above are defined as type-discriminating sites. The type-discriminating site of the present invention consists of all or a part of the sites of unconserved nucleotides in all of the nucleotide sequences of insects of the same morphology from different habitats. The term "unconserved nucleotide" means that all of the nucleotide is not same in a column of the resulting alignment data in the nucleotide sequences of all of the individuals, and even a residue containing a nucleotide change from only one individual is not taken to be conserved. The type-discriminating site in a criterion of the present invention consists of the unconserved nucleotide, but such a nucleotide may be eliminated from the type-discriminating site if it is located at a very unreliable site or a site presumably bearing little relation to habitat properties. The number of nucleotides contained in a type-discriminating site is one or more, preferably 3-50, more preferably 5-30, more preferably 15-30.

(e) Typing Step

Then, nucleotides corresponding to each other in the type-discriminating sites of all of the individuals are compared and classified. That is, completely identical type-discriminating sites are classified as the same type, and incompletely identical type-discriminating sites are classified as one or more different types. Here, the term "completely identical type-discriminating sites" means that all of the nucleotides constituting the type-discriminating site are identical, and the term "incompletely identical type-discriminating sites" means that one or more nucleotides may be different in all of the nucleotides constituting the type-discriminating site. Therefore, one or more different types may exist.

(f) Step of Preparing a Criterion

Finally, the type-discriminating site of each type can be defined as a criterion by determining the habitat of each type classified on the basis of the habitats of insects belonging to each type. Specifically, the habitat presumably corresponding to one type is determined by comprehensive evaluation of geographical relationships between the habitat from which an insect belonging to one type and the habitat from which an insect belonging to another type, the source of an insect belonging to one type such as the collection route, and the like.

In the case of criteria of *Tribolium castaneum* shown in Table 1 below, for example, the habitats from which insects belonging to Japan type 1 are derived are Urawa, Okayama, Chiba and Takarazuka, the habitat from which insects belonging to Japan type 2 are derived is Okinawa, the habitat from which insects belonging to Japan type 3 are derived is also Okinawa, and the habitats from which insects belonging to abroad type 1 are derived is Thailand. Thus, the habitat presumably corresponding to Japan type 1 is determined to be the main island of Japan isolated by sea, whereby the type-discriminating site of Japan type 1 can be defined as a criterion of the main island of Japan. Similarly, the type-discriminating sites of Japan type 2 and Japan type 3 can be defined as a criterion of Okinawa.

It should be noted that the criteria of the present invention can be improved to more accurate criteria by adding fresh sequence data to the previously accumulated sequence data to perform the above step (b) and the subsequent steps for preparing a criterion described above. For example, a criterion of the main island of Japan other than Japan type 1 may be added by adding sequence data of insects inhabiting an area of the main island of Japan other than Urawa, Okayama, Chiba and Takarazuka described above to prepare the criterion. Alternatively, an area corresponding to abroad type 1 may be changed from Thailand to Thailand and the surrounding area by adding sequence data of insects inhabiting geographically unisolated areas surrounding Thailand to prepare the criterion.

<Area-Discriminating Criterion of the Present Invention>

According to the present invention, an area-discriminating criterion for identifying whether or not the habitat of an insect is an area can also be prepared.

As used herein, the term "area-discriminating criterion" refers to a criterion for identifying whether the habitat of an insect is an area or not, as described above, e.g., a criterion allowing for the identification of whether a sample insect is *Tribolium castaneum* inhabiting the main island of Japan or other areas, as an example.

The "area-discriminating criterion" of the present invention can be prepared as follows. That is, a method comprises the steps of comparing nucleotides corresponding to each other in the criteria obtained by the method described in <Method for preparing a criterion of the present invention> above to extract a nucleotide existing in only one type but not in the other types, and preparing an area-discriminating criterion from one or more nucleotides extracted in the preceding step alone or in combination. Any nucleotide existing in only one type but not in the other types can be an area-discriminating criterion of the present invention, but more accurate identification can be provided if the nucleotides in the other types are identical.

As an example of an area-discriminating criterion of the present invention, the 229th nucleotide of the COI region is G in Japan type 1 in contrast to A in the other types among the criteria shown in Table 1 below so that "the 229th nucleotide G" can be an indicator for discriminating Japan type 1 from the other types, i.e., an area-discriminating criterion. Similarly, the 253rd nucleotide T and the 298th nucleotide G of the same region and the 248th nucleotide A of the ND5 region are nucleotides specific to Japan type 1 so that they can be indicators for discriminating Japan type 1 from the other types. In another case, the 22nd nucleotide of the COI region is T in Canada types (abroad type 3 and abroad type 4) while it is A in the other types so that "the 22nd nucleotide T" can be an indicator for discriminating Canada types from the other types, i.e., an area-discriminating criterion. Similarly, the 142nd nucleotide G is also a nucleotide specific to Canada types so that it can be an indicator for discriminating Canada types from the other types. Table 1 shows the results of nucleotide analysis of single nucleotide polymorphisms in the two mitochondrial gene COI region and ND5 region of *Tribolium castaneum*. When these criteria are used, the habitat of a sample of *Tribolium castaneum* is found to be the main island of Japan if (1) one or more of the following criteria are satisfied: the 229th nucleotide of the COI region of the sample of *Tribolium castaneum* is G, the 253rd nucleotide is T and the 298th nucleotide is G, and/or (2) the 248th nucleotide of the ND5 region is A. The habitat of a sample of *Tribolium castaneum* is found to be Canada, if the 22nd nucleotide of the COI region of the sample of *Tribolium castaneum* is T and/or the 142nd nucleotide is G.

According to present invention, one area-discriminating criterion may not identify one area, but multiple area-discriminating criteria may identify one area.

<Method for Identifying the Habitat of an Insect Using a Criteria of the Present Invention>

The present invention also provides a method for identifying the habitat of an insect. Specifically, it provides a method for identifying the habitat of a sample insect, comprising comparing the nucleotide sequence of an area having a criterion of the present invention as defined above and a nucleotide sequence corresponding to the nucleotide sequence of an area having the criterion in a nucleotide sequence obtained from the sample insect, and analyzing whether or not a nucleotide at the site corresponding to the criterion in the nucleotide sequence of the sample is identical with the nucleotide of the criterion, thereby identifying the habitat of the sample.

(a) Comparison of Nucleotide Sequences

In the method for identifying the habitat of an insect using a criterion of the present invention, the nucleotide sequence of an area having the criterion of the present invention is first compared to a nucleotide sequence corresponding to the nucleotide sequence of an area having the criterion in a nucleotide sequence obtained from the sample insect.

Comparison can be performed by visual evaluation or mathematical calculation. Alternatively, a computer program can be used.

A specific comparison method using a computer program for analysis is illustrated below. That is, a criteria table containing a data representing the nucleotide of a criterion obtained by the method described above and a data representing the location of the nucleotide in the nucleotide sequence is stored in advance in a computer on which a computer program for analysis such as SeqScape (ABI) runs. One or more criteria tables may be stored. Then, a sample nucleotide sequence list containing a data representing a nucleotide obtained from the sample insect is stored in the computer. The nucleotide sequence from the sample can be obtained by extracting DNA and analyzing the nucleotide sequence of the sample in the same manner as described in <Method for preparing a criterion of the present invention>, "(a) Step of determining the nucleotide sequences of DNA of one or more insects from two or more habitats" above. In this case, the nucleotide sequence of the sample is prepared to contain the same region as the reference criterion. Then, the computer compares the data representing nucleotides at the corresponding locations in the nucleotide sequences between the sample nucleotide sequence list and the criteria table by referring to the data representing the location in the nucleotide sequence in the criteria table. Comparison can be performed by aligning both nucleotide sequences using the computer program for analysis.

(b) Analysis of Nucleotides of a Criterion and a Sample

In the method for identifying the habitat of an insect using a criterion of the present invention, the habitat of the sample is identified by analyzing whether or not a nucleotide at the site corresponding to the criterion in the nucleotide sequences of the sample is identical with the nucleotide of the criterion after comparison in (a) described above.

Specifically, an analysis is made of whether or not a nucleotide at the site corresponding to the criterion in the nucleotide sequence of the sample is completely identical with the nucleotide of the criterion, and if it is completely identical, it indicates that the sample is an insect from a habitat to which the criterion belongs. Even if it is not completely identical, the habitat of the sample can be expected. For example, the area may be expected to some extent from the habitat of the criterion even if one or a few of the nucleotides of the criterion are not identical but the other nucleotides are identical.

Thus, the habitat of the sample insect can be identified by using a criterion of the present invention. In the case of computer-based analysis, the habitat of the sample insect can be simply and rapidly identified by comparing and analyzing the nucleotide sequence of the sample and the nucleotide sequence of each habitat in turn when the nucleotide sequence of an area having a criterion about multiple habitats has been recorded in advance.

The comparison can be easily made by marking or otherwise labeling a particular nucleotide defined as a criterion. That is, a nucleotide sequence having a colored control nucleotide (criterion) and a nucleotide sequence from a sample are aligned, and then only the colored nucleotide is extracted to prepare a table comparing both. This facilitates identification of whether or not all of the types of nucleotides and their locations are identical, thereby facilitating identification of whether or not the sample insect belongs to the habitat of the criterion. This method is preferable because even multiple samples can be analyzed simultaneously.

<Computer Program for Analysis for Identifying the Habitat of an Insect>

The present invention also provides a computer program for analysis for allowing a computer to execute a procedure for identifying the habitat of an insect of the present invention.

Figure 21:
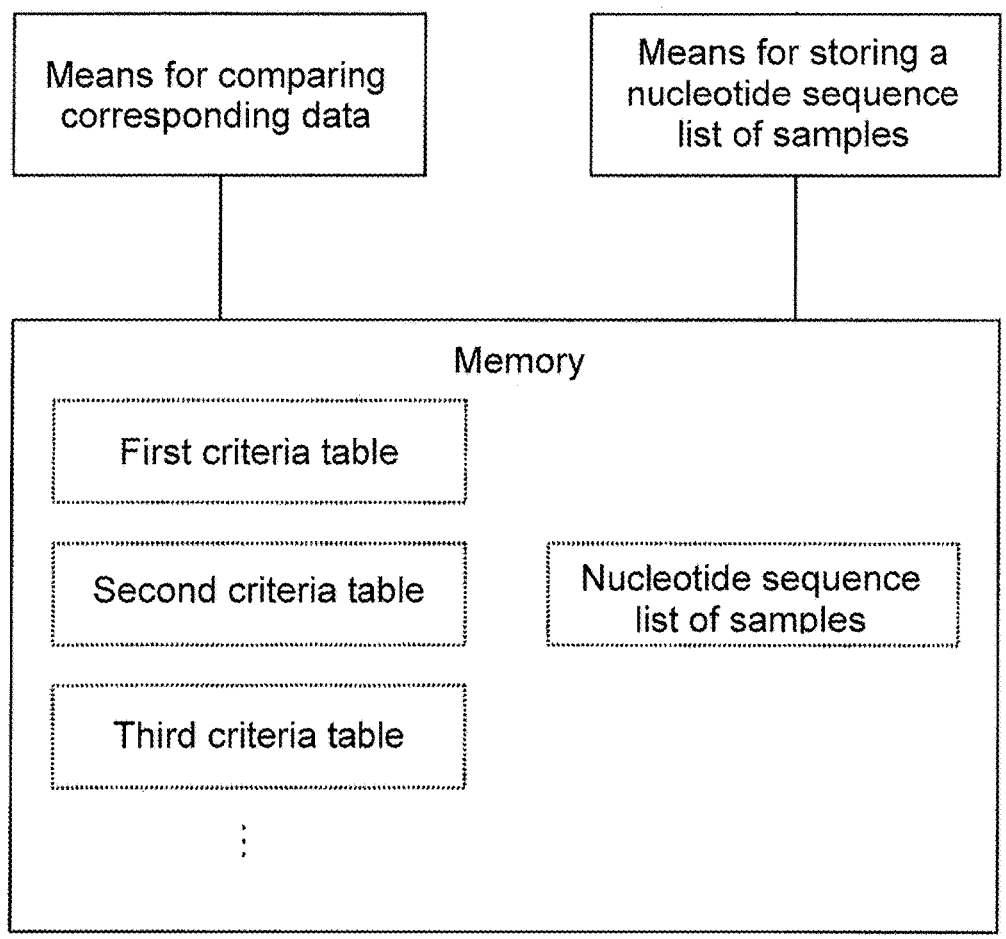
FIG. 21 is a schematic diagram of a computer program for analysis for identifying the habitat of an insect of the present invention.
Figure 22:
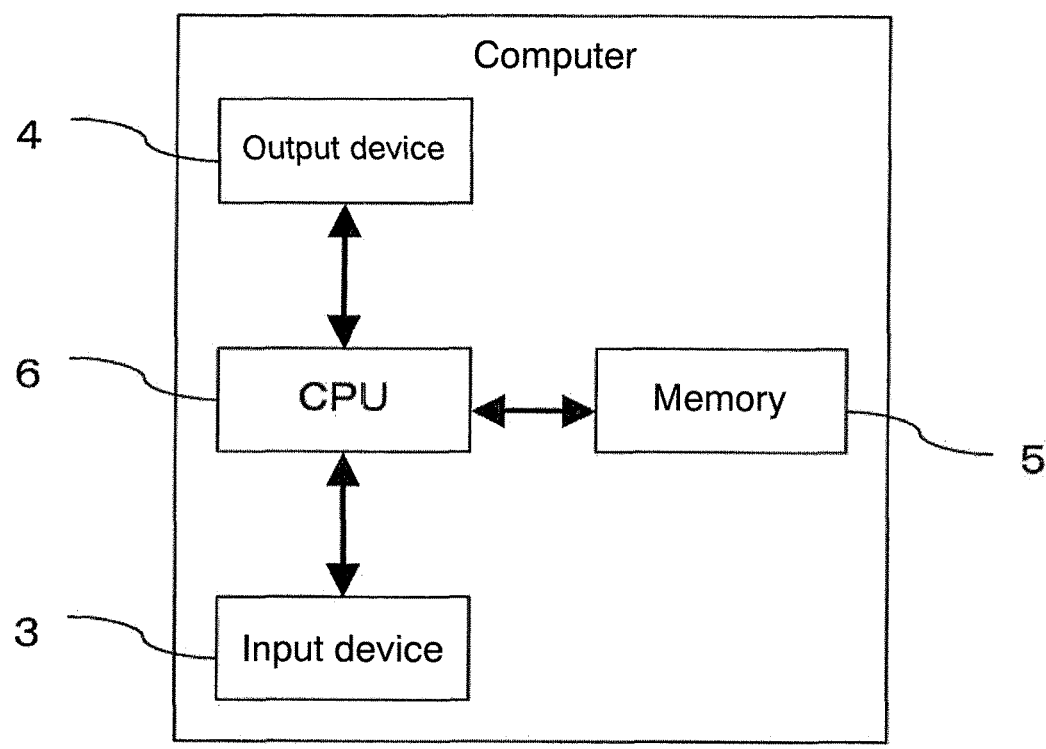
FIG. 22 is a schematic diagram of a computer used with a computer program for analysis for identifying the habitat of an insect.

A computer program for analysis for identifying the habitat of an insect using a criterion of the present invention comprises a criteria table containing a data representing the nucleotide of a criterion, and a data representing the location of the nucleotide in the nucleotide sequence. Specifically, it is a computer program, which allows a host computer used for analysis to function as a means comprising (1) a means for storing a sample nucleotide sequence list containing a data representing a nucleotide obtained from the sample insect, and (2) a means for comparing the data representing nucleotides at the corresponding locations in the nucleotide sequences between the sample nucleotide sequence list and the criteria table by referring to the data representing the location in the nucleotide sequence in the criteria table, thereby directing its hardware resources to cooperate with each other for the purpose of identifying the habitat of the insect (FIG. 21). The computer in the context of the present invention comprises typical hardware resources such as an input device (3), an output device (4), a memory (5), and CPU (6), etc. (FIG. 22). It will be apparent to those skilled in the art that the means of the present invention can be organized by a combination of the hardware resources.

Figure 23:
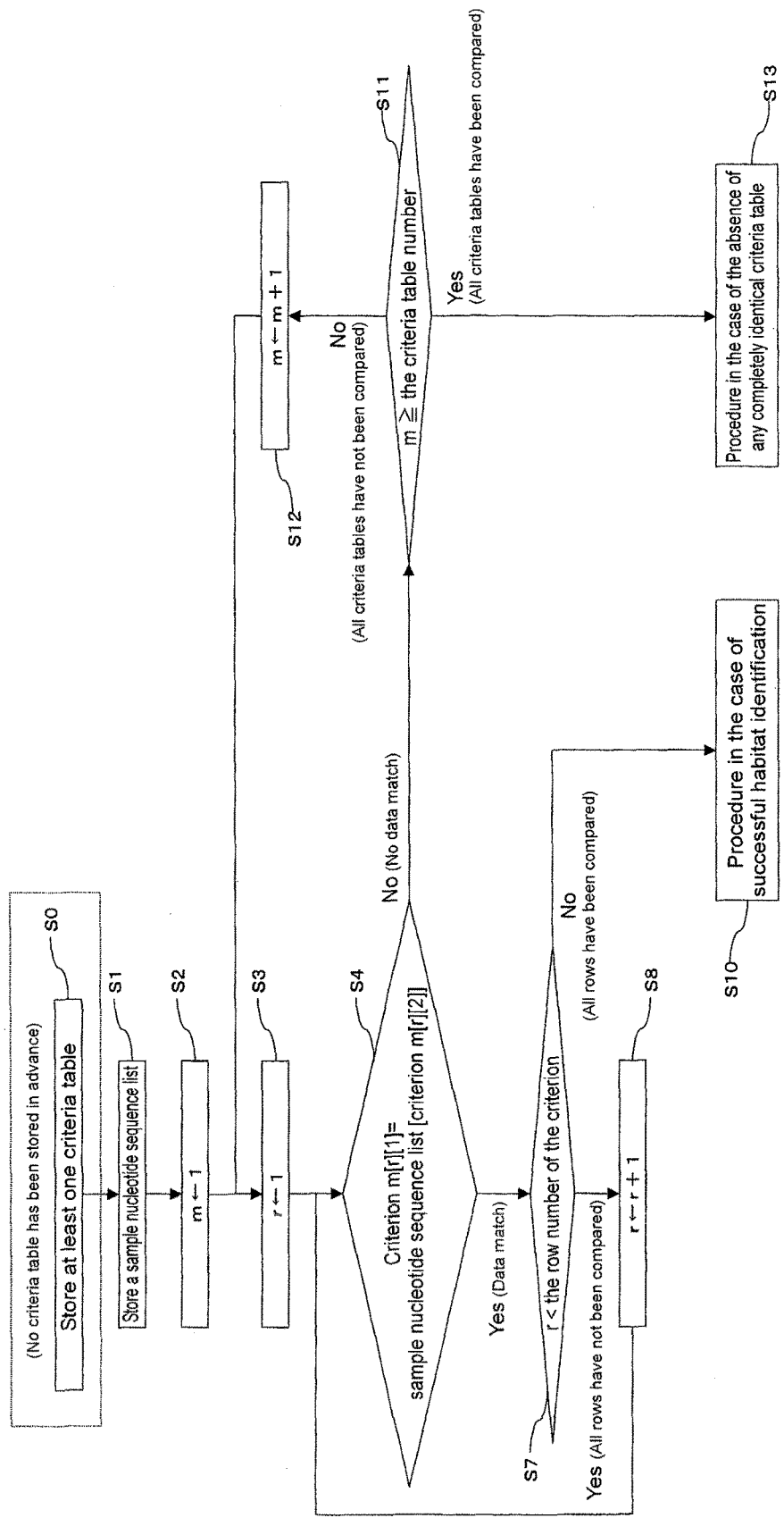
FIG. 23 is a diagram showing that a computer operates with a computer program for analysis for identifying the habitat of an insect.

In order to identify the habitat of an insect using the computer program for analysis of the present invention, it is desirable to provide multiple criteria tables related to various habitats of the insect. Here, one criteria table may be related to only one habitat or more than one habitat. Moreover, the computer program for analysis of the present invention can be stored in a data storage means (ROM, RAM, etc.) to which is accessible a computer connected with a network to allow the computer to function as a means necessary for identifying the habitat and to execute necessary procedures. Thus, the computer program for analysis of the present invention can be described in any programming language functional on a computer used in the present invention or via a network. Specifically, a computer on which a computer program for analysis such as SeqScape (ABI) runs and in which a criterion for each habitat of an insect is stored may be used. Alternatively, the computer program for analysis of the present invention may be a program allowing a computer to operate as follows (FIG. 23). Thus, at least one or more criteria table exist, and have been stored in a memory of the computer in advance or can be stored in it (S0), and can be distinguished from each other by numbers. A criteria table contains a data representing the nucleotide of a criterion in a nucleotide sequence in the first column, and a data representing the location of the nucleotide in the nucleotide sequence in the second column (FIG. 24). For example, the nucleotides A, T, G and C can be encoded into their ASCII codes "A", "T", "G" and "C" and described as data. In the specification and attached drawings, the data in the $r^{th}$ row, the $c^{th}$ column in the $m^{th}$ criteria table is described as "criterion m[c][r]".

(i) A sample nucleotide sequence list is stored in a memory (S1). The sample nucleotide sequence list contains a data representing a nucleotide obtained from the sample insect (FIG. 24). The $n^{th}$ data corresponds to a nucleotide at nucleotide sequence position n. The $n^{th}$ data in the sample nucleotide sequence list is described as "sample nucleotide sequence [n]".

(ii) One of one or more criteria tables is selected. This procedure can be executed by assigning a suitable value (here, value 1) to the variant m representing the number of the criteria table (S2).

(iii) The data in the first column in all rows of the $m^{th}$ criteria table are compared with the data of a corresponding sample nucleotide sequence list. This correspondence relation can be decided by referring to the second column of the criteria table (FIG. 24). This procedure can be executed on a program, for example, by a loop process using the variant r representing the row of a criteria table to be referred to (S3-S8).

(iv) If the comparison of all rows of the $m^{th}$ criteria table in (iii) reveals that the compared data are completely identical, the area related to this criteria table can be identified as the habitat of the sample insect. In this case, a procedure in the case of successful habitat identification is executed (S10). This procedure involves notifying the area related to this criteria table by an output device or the like.

(v) If even one data mismatch appeared during the comparison with the $m^{th}$ criteria table in (iii), the procedure (iii) is repeated on another criteria table (S12). If the procedure has already been repeated on all of the criteria tables (S11), a procedure in the case of the absence of any completely identical criteria table is executed (S13). This procedure involves delivering a relevant message by an output device or the like.

As explained in <Method for identifying the habitat of an insect using a criterion of the present invention> (b), the habitat of a sample can be expected even if the nucleotide sequence of the criterion and the nucleotide sequence of an area corresponding to the criterion of the sample insect are not completely identical. For example, the area may be expected to some extent from the habitat of the criterion even if one or a few of the nucleotides of the criterion are not identical but the other nucleotides are identical. In the computer program for analysis of the present invention, therefore, the habitat of a sample insect can also be identified by executing the procedures above on a conserved region table containing a data representing a nucleotide conserved only in insects of one habitat in a criterion and a data representing the location of the nucleotide in the nucleotide sequence rather than a criteria table. The data structure of this conserved region table is the same as that of the criteria table.

In order to that the computer program for analysis of the present invention runs on a computer, necessary programs for accessing it via typical computer networks such as e.g., well-known operating systems (OSs) or internet browser software are also used in addition to the computer program for analysis of the present invention. Well-known operating systems include, but not limited to, Windows®, Mac OS, Linux, FreeBSD, Solaris, etc.

The computer program for analysis of the present invention allows standard data of criteria for each insect or each habitat or the like and a program for identification using it to be stored by categories. This is preferable because the habitat of a sample can be rapidly identified.

<Computer-Readable Medium>

The computer program for analysis of the present invention can be recorded on a computer-readable medium or a computer-connectable storage means, and can be read as appropriate so that it can run and serve on a computer. Thus, recording media or storage means for computers containing the computer program for analysis of the present invention are also included in the present invention. Such recording media or storage means include, but not limited to, magnetic media such as flexible disks, hard disks, memory storages; optical media such as CD, DVD; magneto-optical media such as MO, MD.

The computer program for analysis of the present invention can be executed and used on a computer by downloading from another computer networked via a data transfer medium or wireless connection. The data transfer medium refers to a communication medium in a computer network system for transmitting program information as a carrier wave to supply the computer program for analysis of the present invention, and such data transfer media include, but not limited to, 10BASE-T cable, 100BASE-TX cable, 1000BASE-TX cable, etc.

The computer program for analysis of the present invention can be implemented on another computer networked via a data transfer medium or wireless connection and used by accessing by a client program running on a computer. Computer network systems include, but not limited to, LAN (Local Area Network), WAN (Wide Area Network) such as internet, MAN (Metropolitan Area Network), intranet, SAN (Storage Area Network), wireless communication network, etc. Communication media include, but not limited to, optical fiber and wireless network, etc. Client programs include, but not limited to, WEB browser, terminal software, client software dedicated for the computer programs for analysis herein, etc.

<Primers and Probes for Use in the Methods for Identifying the Habitat of an Insect>

The present invention also provides primers and probes for used in the method for identifying the habitat of an insect.

A nucleotide specific to one habitat can be selected from those containing a single nucleotide polymorphism of a criterion of the present invention to design a primer and a probe flanking this nucleotide. When the primer and probe are used to amplify DNA from a sample insect as a template by PCR, success of amplification (positive) can be identified as an insect from this habitat while failure of amplification (negative) can be determined as an insect from another habitat. Specifically, the nucleotide specific to one habitat can be selected by the method described in <Area-discriminating criterion of the present invention> above.

For example, single nucleotide polymorphisms are found at the 229th and 298th nucleotides from the 5'-end in the analyzed region of the COI gene of *Tribolium castaneum* in Table 1. That is, these nucleotides are G in Japan type 1 while these nucleotides are A in insects inhabiting other areas than the main island of Japan (hereinafter sometimes referred to as "abroad"). Based on this difference, a primer specific to Japan type 1 (hereinafter sometimes referred to as "primer for the main island of Japan") and a primer specific to abroad (hereinafter sometimes referred to as "primer for abroad") can be designed, as described in the Examples below. Specifically, primers containing nucleic acids shown in SEQ ID NOs: 17-24 shown in Examples below can be designed. These primers are preferable because insects showing positive results for the primer for the main island of Japan and negative results for the primer for abroad can be more accurately identified to inhabit the main island of Japan based on the nucleotide variation A or G in the single nucleotide polymorphism of the present invention. In other words, a nucleotide existing in only one type and not in the other types can be a primer of the present invention, but more accurate identification can be provided if the nucleotides in the other types are identical.

Primers of the present invention specifically also allow for the identification of whether or not *Tribolium castaneum* inhabits the main island of Japan. Specifically, primers identifying whether or not *Tribolium castaneum* inhabits the main island of Japan can be prepared by suitable combination of pairs of the primer described above or modification of a nucleotide contained in each primer. For example, primers containing nucleic acids shown in SEQ ID NOs: 25-29 described in the Examples below and a common primer (3'-end) can be designed on the basis of the finding that the 248th nucleotide from the 5'-end in the analyzed region of the ND5 gene of *Tribolium castaneum* is A in Japan type 1 while it is G in abroad as shown in Table 1. Such primers and probes can be used to prepare primers and probes giving positive results only for Japan type 1, i.e., DNA from insects inhabiting the main island of Japan and negative results for DNA from insects from other areas. For example, such primers giving positive results only for Japan type 1 can be used to identify whether or not the sample insect inhabits the main island of Japan.

<Method for Identifying the Habitat of an Insect Using a Primer or Probe of the Present Invention>

The present invention provides a method for identifying the habitat of an insect using the primers or probes described above. Specifically, the method comprises the steps of: (a) extracting DNA of the sample insect; (b) contacting DNA extracted in said step (a) with a primer and/or a probe of the present invention; (c) amplifying a DNA fragment; and (d) identifying the habitat of the sample insect. Each step is specifically explained below.

(a) The step of extracting DNA of the sample insect can be performed by a method as described in "(2) Extraction of DNA" in <Method for preparing a criterion of the present invention> "(a) Step of determining the nucleotide sequences of DNA of one or more insects from two or more habitats" above.

(b) Step of Contacting the Extracted DNA with a Primer and/or a Probe of the Present Invention Any method for contacting under conditions suitable for PCR amplification reaction can be used, including the use of commercially available kits or the like. For example, a PCR reaction solution (50 μl; 0.2-ml microtube) is prepared by using PerfectShot Ex Taq (Loading dye mix) (Takara Bio Inc.) following the attached manual, and a primer and/or a probe and a template (template DNA) are added to suitable final concentrations to prepare a PCR reaction solution.

(c) Step of Amplifying a DNA Fragment

Known methods may be used for amplifying a DNA fragment. For example, real-time PCR can be used. Any PCR amplification conditions can be used under which a positive control primer and/or a probe and a template are amplified. For example, the PCR reaction solution described above may be used under PCR conditions of denaturation at 94° C. for 3 minutes, followed by 40 cycles of denaturation (94° C., 30 seconds), annealing (55° C., 45 seconds) and elongation (72° C., 60 seconds).

(d) Step of Identifying the Habitat of the Sample Insect

For identifying the habitat of the sample insect, success or failure of amplification by PCR performed in (c) above is evaluated, and the results are analyzed.

Specifically, an adequate amount of the PCR reaction solution obtained above is subjected to agarose gel electrophoresis under suitable condition and then stained in an ethidium bromide solution, and the amplified product is photographed under UV irradiation to evaluate whether or not a desired DNA fragment has been amplified. For example, the expected size of the COI gene of *Tribolium castaneum* is 110 bp in length, and the expected size of the ND5 gene is 139 bp in length. If amplification is successful, a band of the desired DNA fragment can be visually observed, and therefore, if a band is visually observed, DNA derived from the sample is determined to be positive for the primer so that the sample insect can be identified as an insect from the habitat of the primer.

In the present invention, real-time PCR can also be used as step (c) of amplifying a DNA fragment. In this case, a probe and a primer designed and synthesized to flank a nucleotide specific to one habitat selected from nucleotides containing a single nucleotide polymorphism of a criterion of the present invention can be used. For example, Custom TaqMan® Gene Expression/SNP Genotyping Assays service of ABI may be used for designing and synthesizing primers and probes. The principle using this TaqMan® MGB probe from ABI is explained below.

First, a PCR primer set capable of amplifying a region containing a SNP on the genome and two TaqMan® MGB probes corresponding to the single nucleotide variation on the genomic DNA are provided. Fundamentally, the primers, two TaqMan® MGB probes having sequences complementary to allele 1 and allele 2, and template DNA are mixed, and amplified by PCR to detect SNPs of the two alleles. Specifically, the probes used in the present invention are labeled at the 5'-end with a reporter fluorescent dye FAM or VIC, and further conjugated at the 3'-end to a non-fluorescent quencher (NFQ) and Minor Groove Binder (MGB). Upon irradiation with reporter-exciting light (488 nm) in the presence of the probes alone, the reporter fluorescent dye is excited to emit fluorescent light (around 530-560 nm), but the fluorescent wavelength of this reporter is absorbed by the quencher and the quencher does not emit fluorescent light, so that the fluorescence of the reporter is inhibited. When this TaqMan® MGB probe is used for PCR reaction, the probe hybridized with the template DNA together with PCR primers during the elongation step is hydrolyzed by the 5'-3' exonuclease activity of AmpliTaq DNA polymerase. As a result, the reporter fluorescent dye is released to increase the fluorescent strength of the reporter, and the MGB attached to the NFQ penetrates and binds a small groove (gap) where the probe and the template DNA have been hybridized. This enhances binding between the probe and the template DNA to increase the Tm value. The increased Tm value allows more definite identification of a single nucleotide even in a short sequence. The PCR results can be obtained by evaluating success or failure of amplification using a detector for detecting the fluorescent substance conjugated to the probe in advance.

The following examples further illustrate the present invention. However, the present invention is not limited to the Examples below.

Example 1

1. Sequence Data from Insects (A) Insects

The insects used for DNA extraction are the species *Tribolium castaneum* belonging to the family Tenebrionidae in the order Coleoptera, which is most widely known as an insect of the same morphology inhabiting various areas of the world including Japan and very harmful to cereal powders such as flour. The insects of *Tribolium castaneum* used in this example were collected in seven areas where they lived, and were individually raised. They include insects from Chiba collected in a newly built residential house in Chiba Prefecture, insects from Urawa collected in the field of Urawa, insects from Okayama collected in a non-newly built residential house in Okayama Prefecture, insects from Takarazuka purchased from Sumika Technoservice Corporation who collected and raised them in Takarazuka, insects from Okinawa collected in Okinawa Prefecture, insects from Thailand found in cashew nut purchased in Thailand in May, 2006, and insects from Canada found in flour exported from Canada to Hong Kong. For DNA extraction, whole body of these insects were typically used.

(B) DNA Extraction

In the DNA extraction step, the DNA extracted by the CTAB method was amplified by PCR and sequenced to provide sequence data, as explained below.

The CTAB DNA extraction protocol was as follows.

A CTAB solution containing 2% (w/v) CTAB (from Calbiochem), 100 mM Tris-HCl (pH 8.0), 20 mM EDTA (pH 8.0), 1.4 M NaCl, 1% (w/v) PVP (polyvinylpyrrolidone) was prepared. In a microhomogenizer was placed 650 μl of this CTAB solution with insect samples. Then, this microhomogenizer containing the samples and the CTAB solution was incubated in a water bath controlled at 65° C. for 10 minutes in such a manner that the samples in it were immersed. The samples were then milled in the glass tube (having a ground-glass bottom) of the microhomogenizer using a glass rod having a ground-glass round tip (processed to cooperate with the bottom of the glass tube), and then incubated with 2 μl of 1 mg/ml RNase A solution at 65° C. for 1 hour to disrupt cells of the insects. This was transferred to a 1.5-ml microtube, and an equal volume (650 μl) of phenol/chloroform/isoamyl alcohol (25:24:1) was added and the materials were mixed by tumbling by hand for 3 minutes. The mixture was partitioned between an organic solvent layer (lower layer) and an aqueous layer (upper layer) by brief centrifugation (Beckman Allegra 21R Centrifuge F2402H; 15,000 rpm (about 15,000×g) for 1-5 minutes)), and the aqueous layer (about 400 μl) was transferred to a fresh tube. An equal volume of isopropyl alcohol was added and the materials were mixed by tumbling, and then centrifuged in the same manner as described above. The supernatant was discarded and the precipitate was rinsed with 70% ethanol, dried and dissolved in 20-50 μl of TE buffer to prepare a DNA sample.

(C) PCR

For amplifying DNA fragments, a PCR reaction solution (50 μl; 0.2-ml microtube) was prepared using PerfectShot Ex Taq (Loading dye mix) (Takara Bio Inc.) following the attached manual. The amounts (final concentrations) of the primers and templates (template DNA) added and the PCR conditions were as follows.

1) Analysis of the Mitochondrial COI Gene

```
Primer set:
L6625
                                      (SEQ ID NO: 13)
5'-CCGGATCCTTYTGRTTYTTYGGNCAYCC-3' 1 µM H7005
                                      (SEQ ID NO: 14)
5'-CCGGATCCACANCRTARTANGTRTCRTG-3' 1 µM
```

Template: 1 μl/50 μl reaction solution

This microtube was placed in a PCR reactor (DNA Thermal Cycler GeneAmp PCR System 9600 from former Perkin Elmer or TaKaRa PCR Thermal Cycler PERSONAL) to perform PCR amplification under the following conditions:

denaturation: 94° C., 1 minute
annealing: 60° C., 1 minute
elongation: 70° C., 2 minutes.

Fifty cycles of the reaction were run. When the sample could not be collected immediately after completion of the reaction, the temperature of the sample block was lowered to 4° C. and kept at that level.

2) Analysis of the Mitochondrial ND5 Gene

```
Primerset:
F6999
                                      (SEQ ID NO: 15)
5'-AAACAGTTAAAMCARTWGAA-3' 1 µM R7495
                                      (SEQ ID NO: 16)
5'-CCTGTWTCWDCTTTAGTWCA-3' 1 µM
```

Template: 1 μl/50 μl reaction solution

This microtube was placed in a PCR reactor (DNA Thermal Cycler GeneAmp PCR System 9600 from former Perkin Elmer or TaKaRa PCR Thermal Cycler PERSONAL) to perform PCR amplification under the following conditions:

predenaturation: 94° C., 3 minutes
denaturation: 94° C., 30 seconds
annealing: 45° C., 45 seconds
elongation: 72° C., 60 seconds.

Forty cycles of the reaction except for predenaturation were run. When the sample could not be collected immediately after completion of the reaction, the temperature of the sample block was lowered to 4° C. and kept at that level.

(D) Verification of Amplification by PCR

A 5-μl aliquot of the PCR reaction solution obtained above was subjected to agarose gel electrophoresis. In this case, electrophoresis was performed by using Mupid Mini Gel Electrophoresis System (gel: 3% NuSieve 3:1 Agarose from FMC BioProducts or Cambrex Bio Science Rockland, electrophoretic conditions: 100 V, 30 minutes), and the gel was stained in a 2 μg/ml ethidium bromide solution for about 40 minutes, and then, the amplified product was photographed under UV irradiation to verify that a desired DNA fragment (size COI: 435 bp in length, ND5: 513 bp in length) had been amplified (circled bands in FIGS. 1-7 (COI), FIGS. 8-13 (ND5)).

Figure 2:
FIG. 2 is a photograph showing electrophoretic bands of DNA of the mitochondrial COI gene region of *Tribolium castaneum* from Canada 1.
Figure 3:
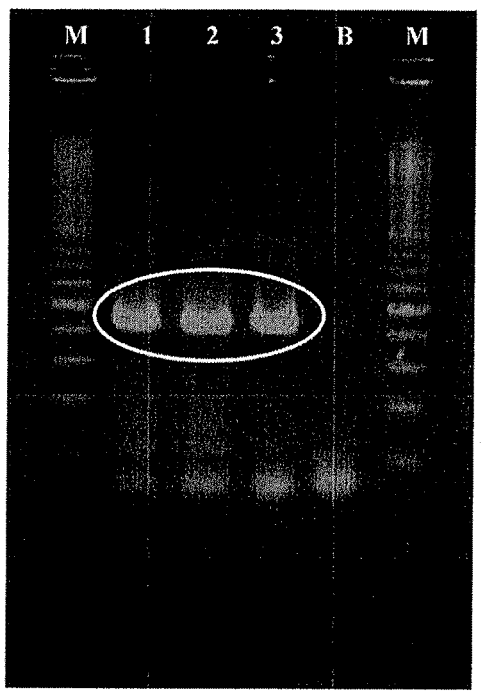
FIG. 3 is a photograph showing electrophoretic bands of DNA of the mitochondrial COI gene region of *Tribolium castaneum* from Chiba 1, Urawa 1 and Okayama 1.
Figure 4:
FIG. 4 is a photograph showing electrophoretic bands of DNA of the mitochondrial COI gene region of *Tribolium castaneum* from Thailand 2 and Thailand 3.
Figure 5:
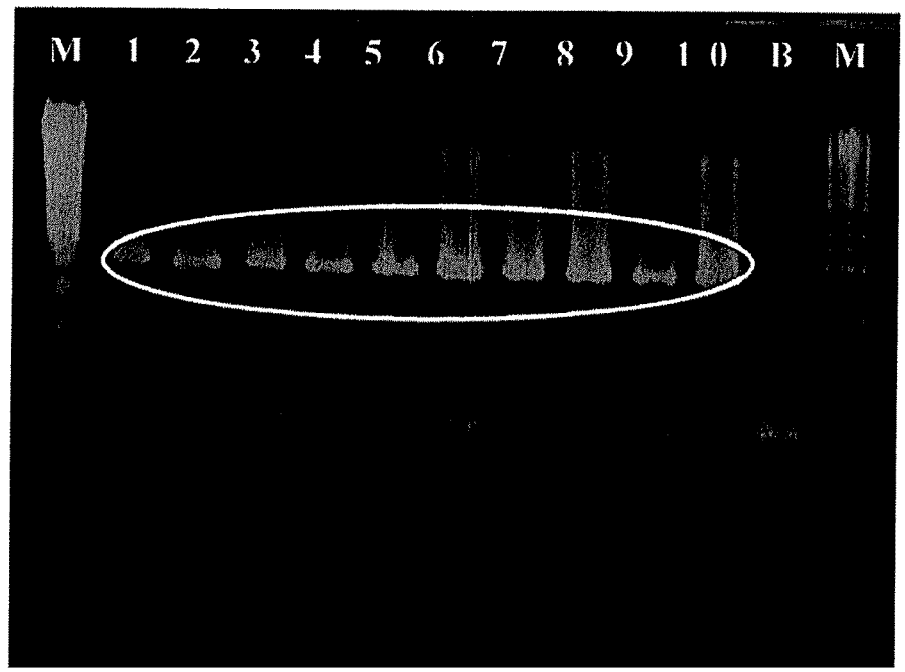
FIG. 5 is a photograph showing electrophoretic bands of DNA of the mitochondrial COI gene region of *Tribolium castaneum* from Canada 2, Canada 3, Okinawa 2, Okinawa 3, Chiba 2, Chiba 3, Okayama 2, Okayama 3, Urawa 2, and Urawa 3.
Figure 6:
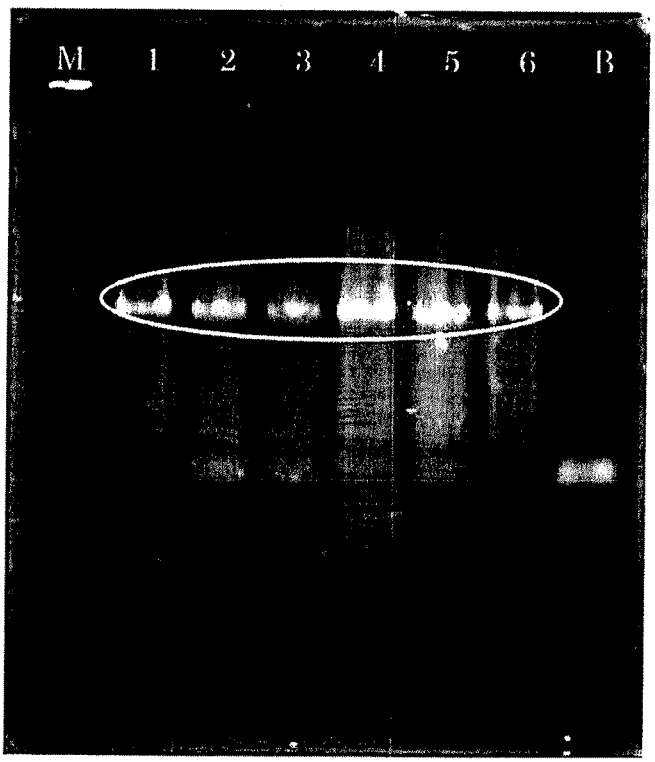
FIG. 6 is a photograph showing electrophoretic bands of DNA of the mitochondrial COI gene region of *Tribolium castaneum* from Thailand 4, Thailand 5, Okinawa 4, Okinawa 5, Canada 4 and Canada 5.
Figure 7:
FIG. 7 is a photograph showing electrophoretic bands of DNA of the mitochondrial COI gene region of *Tribolium castaneum* from Takarazuka 1, Takarazuka 2 and Takarazuka 3.
Figure 8:
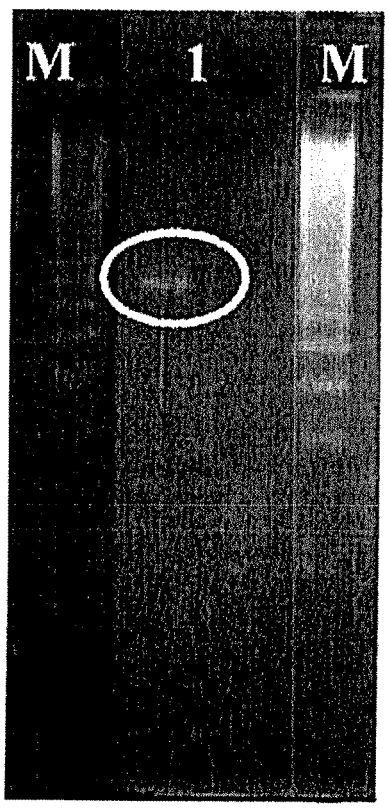
FIG. 8 is a photograph showing electrophoretic bands of DNA of the mitochondrial ND5 gene region of *Tribolium castaneum* from Thailand 1.
Figure 9:
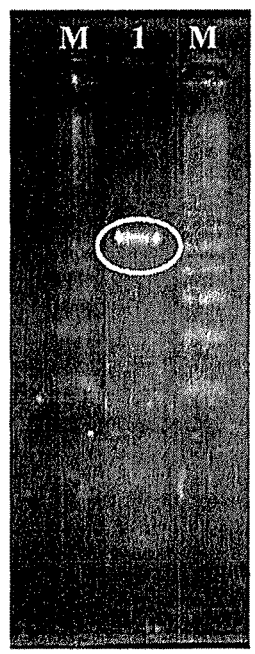
FIG. 9 is a photograph showing electrophoretic bands of DNA of the mitochondrial ND5 gene region of *Tribolium castaneum* from Okinawa 1.
Figure 10:
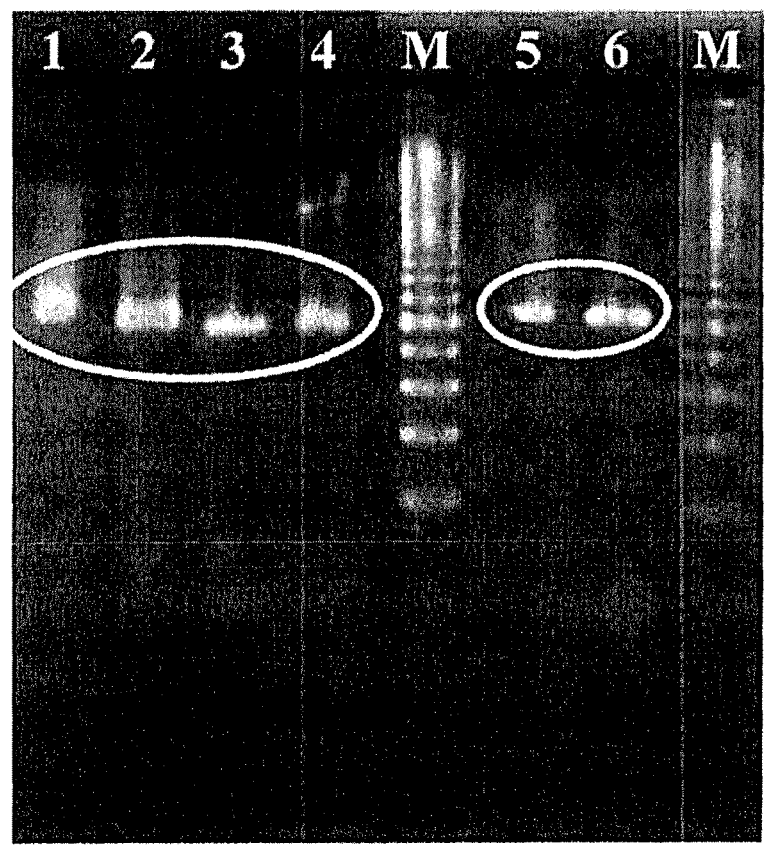
FIG. 10 is a photograph showing electrophoretic bands of DNA of the mitochondrial ND5 gene region of *Tribolium castaneum* from Thailand 2, Thailand 3, Okayama 1, Urawa 1, Chiba 1 and Canada 1.
Figure 11:
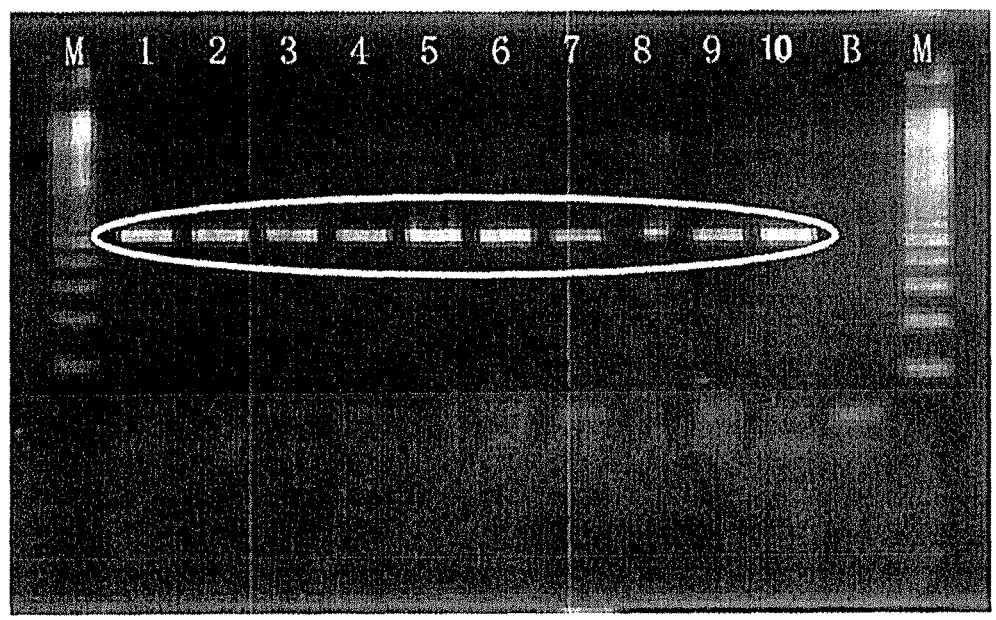
FIG. 11 is a photograph showing electrophoretic bands of DNA of the mitochondrial ND5 gene region of *Tribolium castaneum* from Urawa 2, Urawa 3, Okayama 2, Okayama 3, Chiba 2, Chiba 3, Okinawa 2, Okinawa 3, Canada 2 and Canada 3.
Figure 12:
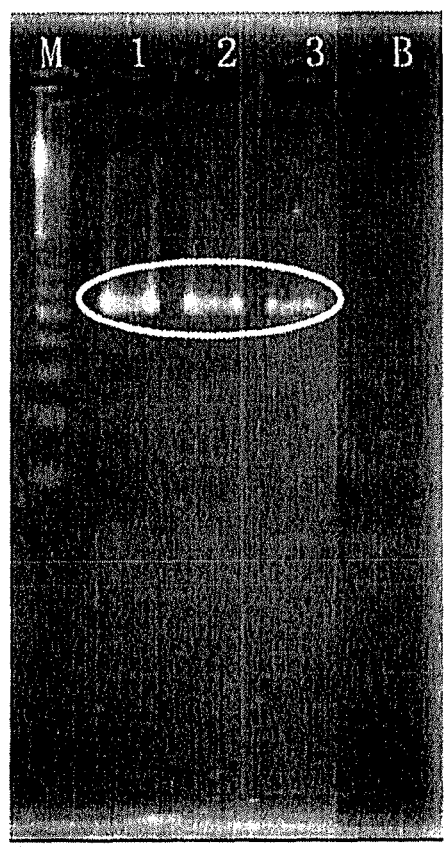
FIG. 12 is a photograph showing electrophoretic bands of DNA of the mitochondrial ND5 gene region of *Tribolium castaneum* from Takarazuka 1, Takarazuka 2 and Takarazuka 3.
Figure 13:
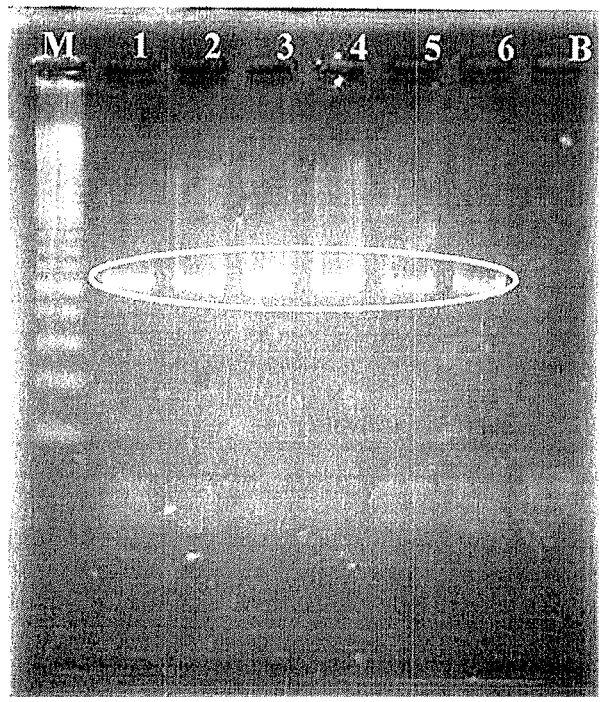
FIG. 13 is a photograph showing electrophoretic bands of DNA of the mitochondrial ND5 gene region of *Tribolium castaneum* from Thailand 4, Thailand 5, Okinawa 4, Okinawa 5, Canada 4 and Canada 5.

In FIG. 1, lane 1 shows *Tribolium castaneum* from Thailand-1, lane 2 shows *Tribolium castaneum* from Okinawa-1, lane B shows a blank without template, and lane M shows a ladder marker of 100 bp in length (100-bp ladder), respectively. In FIG. 2, lane 1 shows *Tribolium castaneum* from Canada-1, lane B shows a blank without template, and lane M shows a size marker (100-bp ladder), respectively. In FIG. 3, lane 1 shows *Tribolium castaneum* from Chiba-1, lane 2 shows *Tribolium castaneum* from Urawa-1, lane 3 shows *Tribolium castaneum* from Okayama-1, lane B shows a blank without template, and lane M shows a size marker (100-bp ladder), respectively. In FIG. 4, lane 1 shows *Tribolium castaneum* from Thailand-2, lane 2 shows *Tribolium castaneum* from Thailand-3, lane B shows a blank without template, and lane M shows a size marker (100-bp ladder), respectively. In FIG. 5, lanes 1-10 show *Tribolium castaneum* from Canada-2, -3, Okinawa-2, -3, Chiba-2, -3, Okayama-2, -3, and Urawa-2, -3, respectively, and lane B shows a blank without template, and lane M shows a size marker (100-bp ladder), respectively. In FIG. 6, lanes 1-6 show *Tribolium castaneum* from Thailand-4, -5, *Tribolium castaneum* from Okinawa-4, -5, and *Tribolium castaneum* from Canada-4, -5, respectively, and lane B shows a blank without template, and lane M shows a size marker (100-bp ladder), respectively. In FIG. 7, lane 1 shows *Tribolium castaneum* from Takarazuka-1, lane 2 shows *Tribolium castaneum* from Takarazuka-2, lane 3 shows *Tribolium castaneum* from Takarazuka-3, lane B shows a blank without template, and lane M shows a size marker (100-bp ladder), respectively. In FIG. 8, lane 1 shows *Tribolium castaneum* from Thailand-1, lane B shows a blank without template, and lane M shows a size marker (100-bp ladder), respectively. In FIG. 9, lane 1 shows *Tribolium castaneum* from Okinawa-1, and lane M shows a size marker (100-bp ladder), respectively. In FIG. 10, lanes 1-6 show *Tribolium castaneum* from Thailand-2, -3, *Tribolium castaneum* from Okayama-1, *Tribolium castaneum* from Urawa-1, *Tribolium castaneum* from Chiba-1, and *Tribolium castaneum* from Canada-1, and lane M shows a size marker (100-bp ladder), respectively. In FIG. 11, lanes 1-10 show *Tribolium castaneum* from Urawa-2, -3, Okayama-2, -3, Chiba-2, -3, Okinawa-2, -3, and Canada-2, -3, lane B shows a blank without template, and lane M shows a size marker (100-bp ladder), respectively. In FIG. 12, lanes 1-3 show *Tribolium castaneum* from Takarazuka-1, -2, -3, lane B shows a blank without template, and lane M shows a size marker (100-bp ladder), respectively. In FIG. 13, lanes 1-6 show *Tribolium castaneum* from Thailand-4, -5, Okinawa-4, -5, and Canada-4, -5, lane B shows a blank without template, and lane M shows a size marker (100-bp ladder), respectively.

(E) Purification of the PCR Products

The above PCR products were purified by using QIAquick PCR Purification Kit (50) (Qiagen) following the manufacturer's protocol as follows. That is, the PCR reaction solution (balance about 45 µl) was mixed with 5 volumes of PBI buffer (225 µl). Then, this solution was placed in QIA quickspin and centrifuged at 13,000 rpm (about 11,000×g) for 1 minute. The filtrate was discarded and 750 µl of PE buffer was added, and then the solution was centrifuged at 13,000 rpm for 1 minute. The filtrate was discarded and the solution was centrifuged again at 14,000 rpm (about 13,000×g) for 1 minute. The filtrate was discarded and the column was transferred to a fresh 1.5-ml microtube, 30 µl of EB buffer was added and the column was allowed to stand for 1 minute and then centrifuged at 13,000 rpm for 2 minutes, and the filtrate was collected as a sample.

(F) Cycle Sequencing Reaction and Purification of the Sequenced Products

The reaction was performed by using BigDye Terminator v1.1 Cycle Sequencing Kit (ABI) following the Japanese protocol ("Cycle sequencing of single-stranded DNA and double-stranded DNA" at p. 22, "Cycle sequencing in GeneAmpPCR System 9700, 9600, 2700, 2400" at p. 25, and "Purification method on spin columns (or spin plates)" at p. 38-40), as follows. The nucleotide sequences of the primers used were the same as those used for the amplification of the desired DNA fragments by PCR. That is, 8 µl of Sequence premix (Big dye) and 3.2 µl each of the primers L6625 and H7005 (for analysis of the COI region) or F6999 and R7495 (for analysis of ND5 region) diluted to 1 µM were added to a 2-µl aliquot of a purified solution of the PCR product diluted to 5-20 ng/µl with sterile distilled water, and the solution was brought to a final volume of 20 µl with sterile distilled water to prepare a cycle sequencing reaction solution. A 0.2-ml microtube (for PCR) containing this solution was placed in a PCR reactor (DNA Thermal Cycler GeneAmp PCR System 9600 from former Perkin Elmer) to perform denaturation (96° C., 1 minute), followed by 25 cycles of denaturation (96° C., 10 seconds), annealing (50° C., 5 seconds) and elongation (60° C., 4 min). When the sample could not be collected immediately after completion of the reaction, the temperature of the sample block was lowered to 4° C. and kept at that level.

The sequenced products were purified through CENTRI-SEP SpinColumn (ABI). That is, the sequenced products (about 20 µl) were added on the center of CENTRI-SEP SpinColumn that had been pretreated by swelling the packing material for 2 hours or more at room temperature, and centrifuged at 2,700 rpm (about 500×g) for 2 minutes above a 1.5-ml microtube, and the solution collected in the microtube was recovered as purified DNA. This solution was dried in vacuo, and then 20 µl of TSR or Hi-Di formamide was added, and the solution was allowed to stand for about 10 minutes and then thoroughly mixed. This solution was transferred to a 0.2-ml microtube (for PCR), denatured (95° C., 2 min) in DNA Thermal Cycler GeneAmp PCR System 9600, immediately quenched in ice, and allowed to stand for 10 minutes or more.

(G) DNA Sequencing

ABI PRISM 310 Genetic Analyzer was used following the "ABI PRISM 310 Genetic Analyzer Operation Manual". That is, the quenched sample was transferred to a sample tube, which was then closed with a septum and placed in a 48-well sample tray. Then, sequencing was performed by the dye terminator method following the operation manual.

(H) Analysis of the Nucleotide Sequences

The sequence data obtained from the 5'-end (on the side of primer L6625 or F6999) and the 3'-end (on the side of primer H7005 or R7495) were verified to determine exact nucleotide sequences. The resulting sequence data were shown below.

1) COI Region (379 bp in Full Length)

Japan type 1 (SEQ ID NO: 1) from Urawa (1-3), Okayama (1-3), Chiba (1-3), and Takarazuka (1-3)

[Formula 1]
```
AGAAGTGTACATTCTAATTCTACCAGGATTTGGCATAATCTCCCACATTATTAGACAAGAAAGAGGAAAGAAAGAAG

CATTTGGAACACTAGGAATAATTTATGCAATAATAGCAATTGGGCTCTTAGGTTTTGTTGTATGAGCCCATCACATA

TTTACCGTAGGAATAGACGTTGATACTCGAGCCTATTTCACTTCAGCCACAATAATTATTGCTGTCCCAACCGGGAT
```

-continued
```
TAAAATTTTTAGATGACTAGCTACTCTTCACGGCACTCAAATTAATTATAGTCCTTCTATAATATGGGCACTAGGAT

TTGTATTCCTATTTACAGTGGGAGGACTAACAGGAGTAATCTTAGCAAATTCATCAATTGATATTATACTT
```

Japan type 2 (SEQ ID NO: 2) from Okinawa (2-5)

[Formula 2]
```
AGAGGTATACATTCTAATTCTACCAGGATTTGGTATAATCTCCCACATTATTAGACAAGAAAGAGGAAAGAAAGAAG

CATTTGGAACACTAGGAATAATTTATGCAATAATAGCAATTGGGCTCTTAGGTTTTGTTGTATGAGCCCATCACATA

TTTACCGTAGGAATAGACGTTGATACTCGAGCCTATTTCACTTCAGCCACAATAATTATTGCTGTCCCAACCGGAAT

TAAAATTTTTAGATGACTAGCCACTCTTCACGGCACTCAAATTAATTATAGTCCTTCTATAATATGAGCACTAGGAT

TTGTATTCCTATTTACAGTGGGGGGACTAACAGGAGTAATCTTAGCAAATTCATCAATTGATATTATACTT
```

Japan type 3 (SEQ ID NO: 3) from Okinawa (1)

[Formula 3]
```
AGAAGTGTACATTCTAATTCTACCAGGATTTGGCATAATCTCCCACATTATTAGACAAGAAAGAGGAAAGAAAGAAG

CATTTGGAACACTAGGAATAATTTATGCAATAATAGCAATTGGGCTCTTAGGTTTTGTTGTATGAGCCCACCACATA

TTTACCGTAGGAATAGACGTTGATACTCGAGCCTATTTCACTTCAGCCACAATAATTATTGCTGTTCCAACCGGAAT

TAAAATTTTTAGATGACTAGCCACTCTTCACGGCACTCAAATTAATTATAGCCCTTCTATAATATGAGCACTAGGAT

TTGTATTCCTATTTACAGTGGGAGGACTAACAGGAGTAATCTTAGCAAATTCATCAATTGACATTATACTT
```

Abroad type 1 (SEQ ID NO: 4) from Thailand (1, 3-5)

[Formula 4]
```
AGAGGTATACATTCTAATTCTACCAGGATTTGGTATAATCTCCCACATTATTAGACAAGAAAGAGGAAAGAAAGAAG

CATTTGGAACACTAGGAATAATTTATGCAATAATAGCAATTGGACTCTTAGGTTTTGTTGTATGAGCCCATCACATA

TTTACCGTAGGAATAGACGTTGATACTCGAGCCTATTTCACTTCAGCCACAATAATTATTGCTGTCCCAACCGGAAT

TAAAATTTTTAGATGACTAGCCACTCTTCACGGCACTCAAATTAATTATAGTCCTTCTATAATATGAGCACTAGGAT

TTGTATTCCTATTTACAGTGGGGGGACTAACAGGAGTAATCTTAGCAAATTCATCAATTGATATTATACTT
```

Abroad type 2 (SEQ ID NO: 5) from Thailand (2)

[Formula 5]
```
AGAAGTGTACATTCTAATTCTACCAGGATTTGGCATAATCTCCCACATTATTAGACAAGAAAGAGGAAAGAAAGAAG

CATTTGGAACACTAGGAATAATTTATGCAATAATAGCAATTGGGCTCTTAGGTTTTGTTGTATGAGCCCACCACATA

TTTACCGTAGGAATAGACGTTGATACTCGAGCCTATTTCACTTCAGCCACAATAATTATTGCTGTTCCAACCGGAAT

TAAAATTTTTAGATGACTAGCCACTCTTCACGGCACTCAAATTAATTATAGCCCTTCTATAATATGAGCACTAGGAT

TTGTATTCCTATTTACAGTGGGAGGACTAACAGGAGTAATCTTAGCAAATTCATCAATTGACATTATACTT
```

Abroad type 3 (SEQ ID NO: 6) from Canada (1, 4, 5)

[Formula 6]
```
AGAGGTGTACATTCTAATTCTTCCAGGATTTGGTATAATCTCCCACATTATTAGACAAGAAAGAGGAAAGAAAGAAG

CATTTGGAACACTAGGAATAATTTATGCAATAATAGCAATTGGGCTCTTAGGTTTTGTTGTATGGGCCCACCACATA

TTTACCGTAGGAATAGACGTTGATACTCGAGCCTATTTCACTTCAGCCACAATAATTATTGCTGTTCCAACCGGAAT

TAAAATTTTTAGATGACTAGCCACTCTTCACGGCACTCAAATTAATTATAGCCCTTCTATAATATGAGCACTAGGAT

TTGTATTCCTATTTACAGTGGGAGGACTAACAGGAGTAATCTTAGCAAATTCATCAATTGATATTATACTT
```

Abroad type 4 (SEQ ID NO: 7) from Canada (2, 3)

[Formula 7]
```
AGAGGTGTACATTCTAATTCTTCCAGGATTTGGCATAATCTCCCACATTATTAGACAAGAAAGAGGAAAGAAAGAAG

CATTTGGAACACTAGGAATAATTTATGCAATAATAGCAATTGGGCTCTTAGGTTTTGTTGTATGGGCCCACCACATA

TTTACCGTAGGAATAGACGTTGATACTCGAGCCTATTTCACTTCAGCCACAATAATTATTGCTGTTCCAACCGGAAT

TAAAATTTTTAGATGACTAGCCACTCTTCACGGCACTCAAATTAATTATAGCCCTTCTATAATATGAGCACTAGGAT

TTGTATTCTTATTTACAGTGGGAGGACTAACAGGAGTAATCTTAGCAAATTCATCAATTGATATTATACTT
```

2) ND5 Region (473 bp in Full Length)
Japan type 1 (SEQ ID NO: 8) from Urawa (1-3), Okayama (1-3), Chiba (1-3), and Takarazuka (1-3)

[Formula 8]
TATAAAATCTTAAGTAACCTATTCTTATAATTTCGGCAACCAAATCCTTTGAATAAAATCCTCTTAAAAATGGTAATC

CGCACAAAGATAAATTTCTAATATTAAAATAAACACAAGTTAAAGGTAAAAACTTAACTAAGCCCCCTATATACCGAA

TATCCTGAAAATCACCAACTCTATGAATAATATTCCCAGCACATATAAACAACAAAGCCTTGAATAAAGCATGAGTCA

ATAAATGGAAGAAAGCTAGTTCATATCTTCCTAAAGACAAAATCATTATTATTAAACCAAGCTGTCTTAAAGTAGAC

AAAGCAATAATTTTCTTCAAATCAAATTCAAATCTCGCCCCTAACCCGGACATAAACATTGTCATTCTAGAAATAAAT

AATAAAAAATATATTAACCACTCATTAAAGCAAAAATTAAAACGAATTAATAAATATACCCCTGCCGTTACTAAAGTA

GAAGAA

Japan type 2 and abroad types 1, 2 (SEQ ID NO: 9) from
Okinawa (2-5) and Thailand (1-5)

[Formula 9]
TATAAAATCTTAAGTAACCTATTCTTATAATTTCGGCAACCAAATCCTTTGAATAAAATCCTCTTAAAAATGGTAATC

CGCACAAAGATAAATTTCTAATATTAAAATAAACACAAGTTAAAGGTAAAAACTTAACTAAGCCCCCTATATACCGAA

TATCCTGAAAATCACCAACTCTATGAATAATATTCCCAGCACATATAAACAACAAAGCCTTGAATAAAGCATGAGTCA

ATAAATGGAAGAAGGCTAGTTCATATCTTCCTAAAGACAAAATCATTATTATTAAACCAAGCTGTCTTAAAGTAGAC

AAAGCAATAATTTTCTTCAAATCAAATTCAAATCTCGCCCCTAACCCGGACATAAACATTGTCATTCTAGAAATAAAT

AATAAAAAATATATTAACCACTCATTAAAGCAAAAATTAAAACGAATTAATAAATATACCCCTGCCGTTACTAAAGTA

GAAGAA

Japan type 3 (SEQ ID NO: 10) from Okinawa (1)

[Formula 10]
TATAAAATCTTAAGTAACCTATTCTTATAATTTCGGCAACCAAATCCTTTGAATAAAATCCTCTTAAAAATGGTAATC

CGCACAAAGATAAATTTCTAATATTAAAATAAACACAAGTTAAAGGTAAAAACTTAACTAAGCCCCCTATATACCGAA

TATCCTGAAAATCACCAACTCTATGAATAATATTCCCAGCACATATAAACAACAAAGCCTTGAATAAAGCATGAGTCA

ATAAATGGAAGAAGGCTAGTTCATATCTTCCTAAAGACAAAATCATTATTATTAAACCAAGCTGTCTTAAAGTCGAC

AAAGCAATAATTTTCTTCAAATCAAATTCAAATCTCGCCCCTAACCCAGACATAAACATTGTCATTCTAGAAATAAAT

AATAAAAAATATATTAACCACTCATTAAAACAAAAATTAAAACGAATTAATAAATATACCCCTGCCGTTACTAAAGTA

GAAGAA

Abroad type 3 (SEQ ID NO: 11) from Canada (1, 4, 5)

[Formula 11]
TATAAAATCTTAAGTAACCTATTCTTATAATTTCGGCAACCAAATCCTTTGAATAAAATCCTCTTAAAAATGGTAATC

CGCACAAAGATAAATTTCTAATATTAAAATAAACACAAGTTAAAGGTAAAAACTTAACTAAGCCCCCTATATACCGAA

TATCCTGAAAATCACCAACTCTATGAATAATATTCCCAGGACATATAAACAACAAAGCCTTGAATAAAGCATGAGTCA

ATAAATGGAAGAAGGCTAGTTCATATCTTCCTAAAGACAAAATCATTATTATTAAACCAAGCTGTCTTAAAGTCGAC

AAAGCAATAATTTTCTTCAAATCAAATTCAAATCTCGCCCCTAACCCGGACATAAACATTGTCATTCTAGAAATAAAT

AATAAAAAATATATTAACCACTCATTAAAGCAAAAATTAAAACGAATTAATAAATATACCCCTGCCGTTACTAAAGTA

GAAGAA

Abroad type 4 (SEQ ID NO: 12) from Canada (2, 3)

[Formula 12]
TATAAAATCTTAAGTAACCTATTCTTATAATTTCGGCAACCAAATCCTTTGAATAAAATCCTCTTAAAAATGGTAATC

CGCACAAAGATAAATTTCTAATATTAAAATAAACACAAGTTAAAGGTAAAAACTTAACTAAGCCCCCTATATACCGAA

TATCCTGAAAATCACCAACTCTATGAATAATATTCCCAGCACACATAAACAACAAAGCCTTGAATAAAGCATGAGTCA

-continued

```
ATAAATGGAAGAAGGCTAGTTCATATCTTCCTAAAGACAAAATCATTATTATTAAACCAAGCTGTCTTAAAGTCGAC

AAAGCAATAATTTTCTTCAAATCAAATTGAAATCTCGCCCCTAACCCGGACATAAACATTGTCATTCTAGAAATAAAT

AATAAAAAATATATTAACCACTCATTAAAGCAAAAATTAAAACGAATTAATAAATATACCCCTGCCGTTACTAAAGTA

GAAGAA
```

The above nucleotide sequences in each region (COI or ND5) were compared using a computer program for analysis such as ClustalW2 of EMBL-EBI on the Internet (multiple alignment analysis). As a result, 15 and 5 single nucleotide polymorphisms (SNPs) hatched in the sequences shown above were found in the COI region and ND5 region, respectively. The sequences can be classified in seven types by combining these polymorphisms, and the habitats corresponding to these types were identified as the main island of Japan, Okinawa, Thailand, and Canada by comprehensive evaluation from the source areas of insects belonging to each type and the like. That is, it was determined that Japan type 1 (a total of 12 individuals formed of 3 individuals from each area of Urawa, Okayama, Chiba and Takarazuka; haplotype I-1 (hereinafter indicated in the order of COI-ND5)) primarily covers the main island of Japan; Japan type 2 (4 individuals from Okinawa area; II-2) and Japan type 3 (1 individual from Okinawa area; III-3 (type L)) primarily cover Okinawa; abroad type 1 (4 individuals from Thailand area; IV-2) and abroad type 2 (1 individual from Thailand area; III-2) primarily cover Thailand; and abroad type 3 (3 individuals from Canada area; V-4) and abroad type 4 (2 individuals from Canada area; VI-5) primarily cover Canada (Table 1). It is also shown that two haplotypes exist in each area except for the nucleotides from the main island of Japan. For example, such a relation exists between Okinawa 2-5 of Japan type 2 and Okinawa 1 of Japan type 3; Thailand 1, 3-5 of abroad type 1 and Thailand 2 of abroad type 2; Canada 1, 4, 5 of abroad type 3 and Canada 2, 3 of abroad type 4 in Table 1 shown below.

TABLE 1

Results of analysis of polymorphisms between habitats of Tribolium castaneum

| Type | Habitat | Source area of individual | COI_L6625/H7005 region: 379 bp in full length Position counted from the 5'-end (number of nucleotides) | | | | | | | | | | | |
|---|---|---|---|---|---|---|---|---|---|---|---|---|---|---|
| | | | 4 | 7 | 22 | 34 | 121 | 142 | 148 | 220 | 229 | 253 | 283 | 298 |
| Japan type 1 | Main island of Japan | Urawa 1 | A | G | A | C | G | A | T | C | G | T | T | G |
| | | Urawa 2 | A | G | A | C | G | A | T | C | G | T | T | G |
| | | Urawa 3 | A | G | A | C | G | A | T | C | G | T | T | G |
| | | Okayama 1 | A | G | A | C | G | A | T | C | G | T | T | G |
| | | Okayama 2 | A | G | A | C | G | A | T | C | G | T | T | G |
| | | Okayama 3 | A | G | A | C | G | A | T | C | G | T | T | G |
| | | Chiba 1 | A | G | A | C | G | A | T | C | G | T | T | G |
| | | Chiba 2 | A | G | A | C | G | A | T | C | G | T | T | G |
| | | Chiba 3 | A | G | A | C | G | A | T | C | G | T | T | G |
| | | Takarazuka 1 | A | G | A | C | G | A | T | C | G | T | T | G |
| | | Takarazuka 2 | A | G | A | C | G | A | T | C | G | T | T | G |
| | | Takarazuka 3 | A | G | A | C | G | A | T | C | G | T | T | G |
| Japan type 2 | Okinawa | Okinawa 2 | G | A | A | T | G | A | T | C | A | C | T | A |
| | | Okinawa 3 | G | A | A | T | G | A | T | C | A | C | T | A |
| | | Okinawa 4 | G | A | A | T | G | A | T | C | A | C | T | A |
| | | Okinawa 5 | G | A | A | T | G | A | T | C | A | C | T | A |
| Japan type 3 | | Okinawa 1 | A | G | A | C | G | A | C | T | A | C | C | A |
| Abroad type 1 | Thailand | Thailand 1 | G | A | A | T | A | A | T | C | A | C | T | A |
| | | Thailand 3 | G | A | A | T | A | A | T | C | A | C | T | A |
| | | Thailand 4 | G | A | A | T | A | A | T | C | A | C | T | A |
| | | Thailand 5 | G | A | A | T | A | A | T | C | A | C | T | A |
| Abroad type 2 | | Thailand 2 | A | G | A | C | G | A | C | T | A | C | C | A |
| Abroad type 3 | Canada | Canada 1 | G | G | T | T | G | G | C | T | A | C | C | A |
| | | Canada 4 | G | G | T | T | G | G | C | T | A | C | C | A |
| | | Canada 5 | G | G | T | T | G | G | C | T | A | C | C | A |
| Abroad type 3 | | Canada 2 | G | G | T | C | G | G | C | T | A | C | C | A |
| | | Canada 3 | G | G | T | C | G | G | C | T | A | C | C | A |

TABLE 1-continued

| Type | Habitat | Source area of individual | COI_L6625/H7005 region: 379 bp in full length Position counted from the 5'-end (number of nucleotides) | | | | ND5_L6999/R6495 region: 473 by in full length Position counted from the 5'-end (number of nucleotides) | | | | | | CO I +ND5 |
|---|---|---|---|---|---|---|---|---|---|---|---|---|---|
| | | | 317 | 331 | 370 | type | 200 | 248 | 308 | 359 | 419 | type | type |
| Japan type 1 | Main island of Japan | Urawa 1 | C | A | T | I | T | A | A | G | G | 1 | J |
| | | Urawa 2 | C | A | T | I | T | A | A | G | G | 1 | J |
| | | Urawa 3 | C | A | T | I | T | A | A | G | G | 1 | J |
| | | Okayama 1 | C | A | T | I | T | A | A | G | G | 1 | J |
| | | Okayama 2 | C | A | T | I | T | A | A | G | G | 1 | J |
| | | Okayama 3 | C | A | T | I | T | A | A | G | G | 1 | J |
| | | Chiba 1 | C | A | T | I | T | A | A | G | G | 1 | J |
| | | Chiba 2 | C | A | T | I | T | A | A | G | G | 1 | J |
| | | Chiba 3 | C | A | T | I | T | A | A | G | G | 1 | J |
| | | Takarazuka 1 | C | A | T | I | T | A | A | G | G | 1 | J |
| | | Takarazuka 2 | C | A | T | I | T | A | A | G | G | 1 | J |
| | | Takarazuka 3 | C | A | T | I | T | A | A | G | G | 1 | J |
| Japan type 2 | Okinawa | Okinawa 2 | C | G | T | II | T | G | A | G | G | 2 | K |
| | | Okinawa 3 | C | G | T | II | T | G | A | G | G | 2 | K |
| | | Okinawa 4 | C | G | T | II | T | G | A | G | G | 2 | K |
| | | Okinawa 5 | C | G | T | II | T | G | A | G | G | 2 | K |
| Japan type 3 | | Okinawa 1 | C | A | C | III | T | G | C | A | A | 3 | L |
| Abroad type 1 | Thailand | Thailand 1 | C | G | T | IV | T | G | A | G | G | 2 | M |
| | | Thailand 3 | C | G | T | IV | T | G | A | G | G | 2 | M |
| | | Thailand 4 | C | G | T | IV | T | G | A | G | G | 2 | M |
| | | Thailand 5 | C | G | T | IV | T | G | A | G | G | 2 | M |
| Abroad type 2 | | Thailand 2 | C | A | C | III | T | G | A | G | G | 2 | N |
| Abroad type 3 | Canada | Canada 1 | C | A | T | V | T | G | C | G | G | 4 | O |
| | | Canada 4 | C | A | T | V | T | G | C | G | G | 4 | O |
| | | Canada 5 | C | A | T | V | T | G | C | G | G | 4 | O |
| Abroad type 3 | | Canada 2 | T | A | T | VI | C | G | C | G | G | 5 | P |
| | | Canada 3 | T | A | T | VI | C | G | C | G | G | 5 | P |

Further detailed analysis revealed area-specific characteristics as follows. Japan type 1 refers to a type primarily inhabiting the main island of Japan and characterized by G at positions 229 and 298 and T at position 253 counted from the 5'-end of the COI gene, and A at position 248 of the ND5 region. Japan type 2 and Japan type 3 refer to types primarily inhabiting Okinawa area, but are shown to closely similar to DNA from abroad type 1 inhabiting Thailand area, suggesting a close relation therebetween also from geographical point of view. Abroad type 1 and abroad type 2 agree with Japan type 1 except for G at position 248 of the ND5 gene region. Abroad type 3 and abroad type 4 refer to types primarily inhabiting Canada area and characterized by T at position 22 and G at position 142 of the COI gene region.

2. Development of Primers Used in the Method for Identifying Whether or not the Habitat of *Tribolium castaneum* is the Main Island of Japan Nucleotide changes were found at positions 229 and 298 counted from the 5'-end in the analyzed COI region. That is, these nucleotides are G in Japan type 1, while these nucleotides are A in types inhabiting abroad areas including Okinawa. On the basis of this difference, primers specific to boxed stretches in the nucleotide sequence below were designed.

[Formula 13]
COI region (379 bp in full length shown in the direction of 5' →3'
Japan type 1 (SEQ ID NO: 1): (from Urawa (1-3), Okayama (1-3), Chiba (1-3), Takarazuka (1-3))
AGAAGTGTACATTCTAATTCTACCAGGATTTGGCATAATCTCCCACATTATTAGACAAGAAAGAGGAAAGAAAGAAG

CATTTGGAACACTAGGAATAATITATGCAATAATAGCAATTGGGCTCTTAGGTTTTGTTGTATGAGCCCATCACATA

TTTACCGTAGGAATAGACGTTGATACTCGAGCCTATTTCACTTCAGCCACAAT AATTATTGCTGTCCCAACCGGGAT

TAAAATTTTTAGATGACTAGCTACTCTTCACGGCACTCAAATTAATTATAGTCCTTCTATAATATG GGCACTAGGAT

TTGTATTCC TATTTACAGTGGGAGGACTAACAGGAGTAATCTTAGCAAATTCATCAATTGATATTATACTT

The primers designed are shown below.
Primers for KN discrimination and improved primers

```
Honndo-F   AATTATTGCTGTCCCAACCGGG     (SEQ ID NO: 17)
Honndo-F2  AATTATTGCTGTCCCAACCGAG     (SEQ ID NO: 18)
Honndo-R   GGAATACAAATCCTAGTGCC       (SEQ ID NO: 19)
Honndo-R2  GGAATACAAATCCTAGTGAC       (SEQ ID NO: 20)
Kaigai-F   AATTATTGCTGTYCCAACCGGA     (SEQ ID NO: 21)
Kaigai-F2  AATTATTGCTGTYCCAACCGAA     (SEQ ID NO: 22)
Kaigai-R   RGAATACAAATCCTAGTGCT       (SEQ ID NO: 23)
Kaigai-R2  RGAATACAAATCCTAGTGAT.      (SEQ ID NO: 24)
```

Similarly, primers specific to boxed stretches and a common primer (3'-end) were designed on the basis of A at position 248 in the analyzed ND5 region in Japan type 1 in contrast to G from abroad areas (see the nucleotide sequence of the ND5 region below).

[Formula 14]
```
ND5 region (473 by in full length shown in the direction of 5'
→3',
Japan type 1 (SEQ ID NO: 8): (from Urawa (1-3), Okayama (1-3),
Chiba (1-3), Takarazuka (1-3))
TATAAAATCTTAAGTAACCTATTCTTATAATTTCGGCAACCAAATCCTTTGAATAAAATCCTCTTAAAAATGGTAATC

CGCACAAAGATAAATTTCTAATATTAAAATAAACACAAGTTAAAGGTAAAAACTTAACTAAGCCCCCTATATACCGAA

TATCCTGAAAATCACCAACTCTATGAATAATATTCCCAGCACATATAAACAACAAAGCCTTGAATAAAGCAT|GAGTC|

|AATAAATGGAAGAAA|GCTAGTTCATATCTTCCTAAAGACAAAATCATTATTATTAAACCAAGCTGTCTTAAAGTAGA

CAAAGCAATAATTTTCTTCAAATCAAATTCAAAT|CTCGCCCCTAACCCGGACATAAA|CATTGTCATTCTAGAAATAA

ATAATAAAAAATATATTAACCACTCATTAAAGCAAAAATTAAAACGAATTAATAAATATACCCCTGCCGTTACTAAAG

TAGAAGAA
```

```
ND-Honndo-F    GAGTCAATAAATGGAAGAAA       (SEQ ID NO: 25)
ND-Honndo-F2   GAGTCAATAAATGGAAGATA       (SEQ ID NO: 26)
ND-Kaigai-F    GAGTCAATAAATGGAAGAAG       (SEQ ID NO: 27)
ND-Kaigai-F2   GAGTCAATAAATGGAAGATG       (SEQ ID NO: 28)
ND-Kyoutsuu-R  TTTATGTCCGGGTTAGGGGCGAG.   (SEQ ID NO: 29)
```

PCR

For amplifying DNA fragments, a PCR reaction solution (50 µl; 0.2-ml microtube) was prepared using PerfectShot Ex Taq (Loading dye mix) (Takara Bio Inc.) following the attached manual. The amounts (final concentrations) of the primers and templates (template DNA) added and the PCR conditions were as follows.

Primers:
Combinations of Forward primer (1 µM)/Reverse primer (1 µM)
 1. Honndo-F/Honndo-R
 2. Kaigai-F/Kaigai-R
 3. ND-Honndo-F/ND-Kyoutsuu-R
 4. ND-Kaigai-F/ND-Kyoutsuu-R
Template: 1 µl/50 µl reaction solution
 1. DNA extracted from Urawa (1) as a representative of the main island of Japan.
 2. DNA extracted from Canada (1) as a representative of abroad areas.

This microtube was placed in a PCR reactor (DNA Thermal Cycler GeneAmp PCR System 9600 from former Perkin Elmer or TaKaRa PCR Thermal Cycler PERSONAL) to perform PCR amplification under the following conditions:

predenaturation: 94° C., 3 minutes
denaturation: 94° C., 30 seconds
annealing: 45° C., 45 seconds
elongation: 72° C., 60 seconds.

Forty cycles of the reaction except for predenaturation were run. When the sample could not be collected immediately after completion of the reaction, the temperature of the sample block was lowered to 4° C. and kept at that level.

Figure 14:
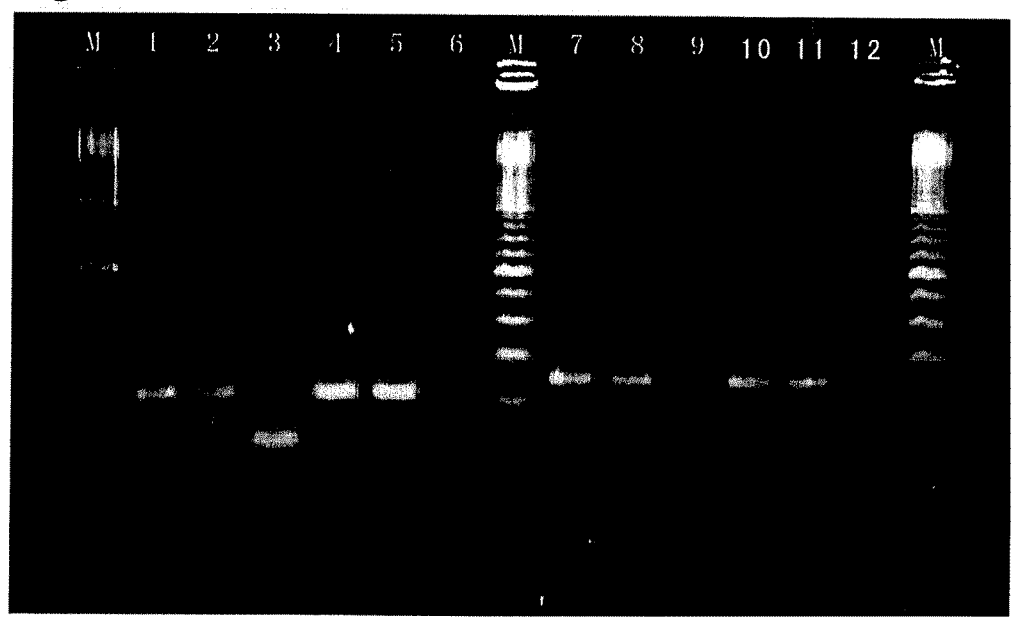
FIG. 14 is a photograph showing electrophoretic bands of DNA of a mitochondrial region of *Tribolium castaneum* from Takarazuka 1 and Canada 1 using different combinations of primers.

3. Evaluation of Success or Failure of Amplification by PCR and Analysis of the Results Five µl of the PCR reaction solution obtained above was subjected to agarose gel electrophoresis. In this case, electrophoresis was performed by using Mupid Mini Gel Electrophoresis System (gel: 3% NuSieve 3:1 Agarose from FMC BioProducts or Cambrex Bio Science Rockland, electrophoretic conditions: 100 V, 30 minutes), and the gel was stained in a 2 µg/ml ethidium bromide solution for about 40 minutes, and then, the amplified product was photographed under UV irradiation to evaluate whether or not a desired DNA fragment (expected size COI: 110 bp in length, ND5: 139 bp in length) had been amplified (FIG. 14). In FIG. 14, the legend for each lane is shown below.

TABLE 2

| | | | |
|---|---|---|---|
| 1 | Urawa-1 | } | |
| 2 | Canada-1 | } | with Honndo-F/Honndo-R |
| 3 | Blank | } | |
| 4 | Urawa-1 | } | |
| 5 | Canada-1 | } | with Kaigai-F/Kaigai-R |
| 6 | Blank | } | |
| 7 | Urawa-1 | } | |
| 8 | Canada-1 | } | with ND-Honndo-F/ND-Kyoutsuu-R |
| 9 | Blank | } | |

TABLE 2-continued

| 10 | Urawa-1  | }  with ND-Kaigai-F/ND-Kyoutsuu-R |
| 11 | Canada-1 | |
| 12 | Blank    | |

The results showed that the expected amplified products were observed in lanes 1, 5, 7, 11, but similar bands were observed in lanes 2, 4, 8, 10 that had been expected to be negative.

Figure 15:
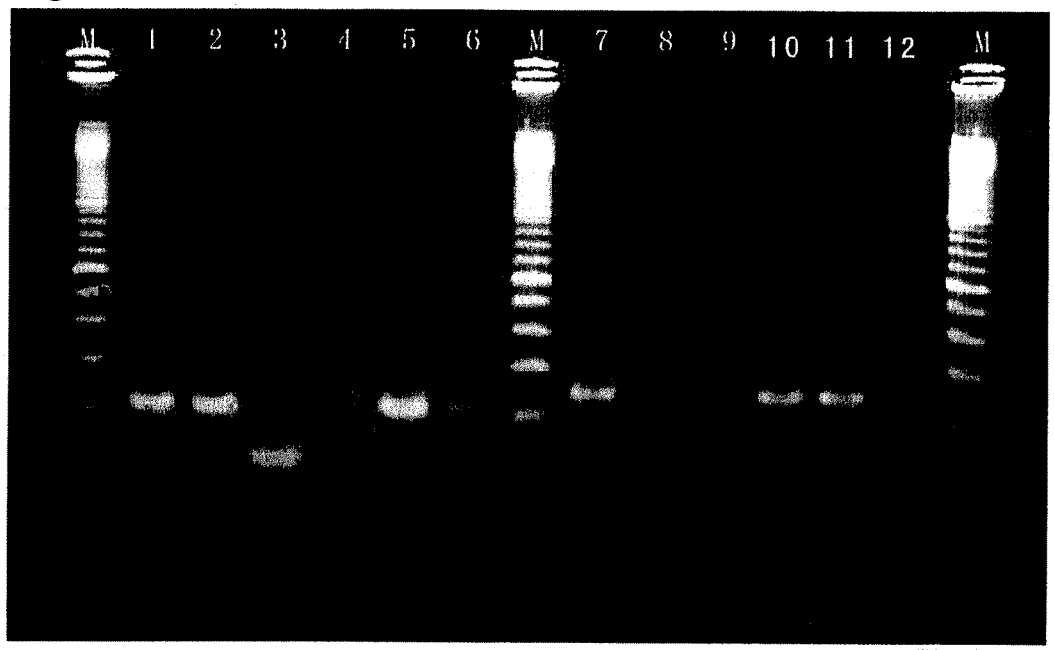
FIG. 15 is a photograph showing electrophoretic bands of DNA of a mitochondrial region of *Tribolium castaneum* from Takarazuka 1 and Canada 1 using different combinations of primers.

When PCR was performed by changing the annealing temperature in the above PCR conditions from 45° C. to 55° C., the bands in lanes 4 and 8 weakened, but the bands in lanes 2 and 10 were as strong as positive bands (lanes 1 and 11) (FIG. 15). In FIG. 15, the legend for each lane is as shown in Table 2.

Then, primers were synthesized with slightly decreased specificity by replacing the nucleotide next to the 3'-end by A or T as described above. These were also combined as described below to perform PCR.

Figure 16:
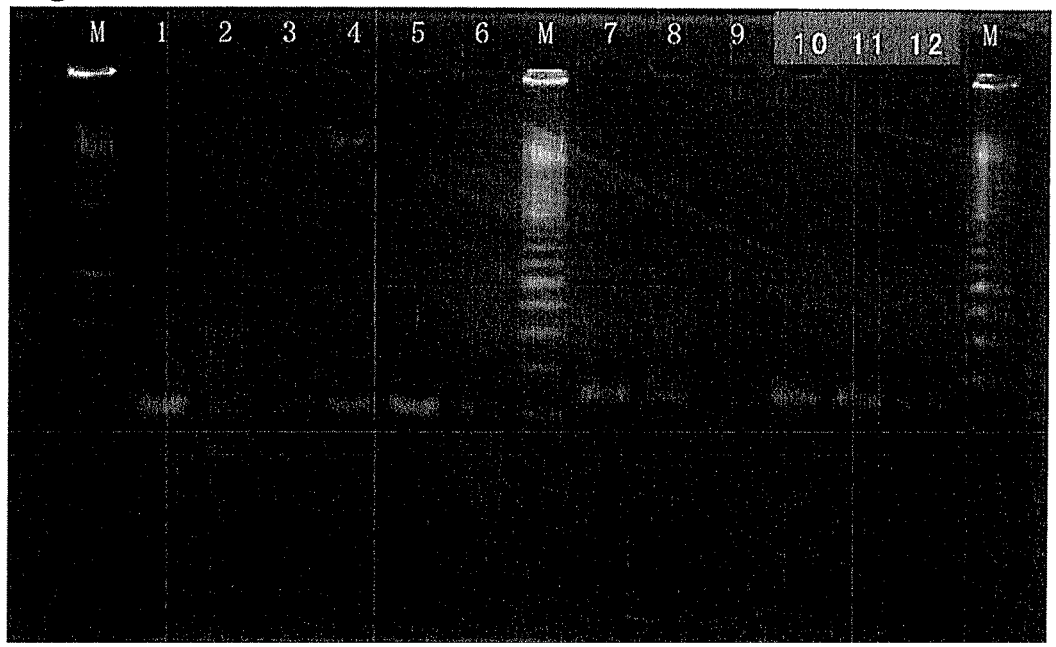
FIG. 16 is a photograph showing electrophoretic bands of DNA of a mitochondrial region of *Tribolium castaneum* from Takarazuka 1 and Canada 1 using different combinations of primers.

Combinations of Forward primer (1 µM)/Reverse primer (1 µM)
1. Honndo-F2/Honndo-R2
2. Kaigai-F2/Kaigai-R2
3. ND-Honndo-F2/ND-Kyoutsuu-R
4. ND-Kaigai-F2/ND-Kyoutsuu-R As a result, the band in lane 2 disappeared, showing a great contrast to lane 1 (FIG. 16). That is, a condition could be found under which Japan type 1 is positive while abroad types are negative. In FIG. 16, the legend for each lane is shown in the table below.

TABLE 3

| 1  | Urawa-1  | }  with Honndo-F2/Honndo-R2 |
| 2  | Canada-1 | |
| 3  | Blank    | |
| 4  | Urawa-1  | }  with Kaigai-F2/Kaigai-R2 |
| 5  | Canada-1 | |
| 6  | Blank    | |
| 7  | Urawa-1  | }  with ND-Honndo-F2/ND-Kyoutsuu-R |
| 8  | Canada-1 | |
| 9  | Blank    | |
| 10 | Urawa-1  | }  with ND-Kaigai-F2/ND-Kyoutsuu-R |
| 11 | Canada-1 | |
| 12 | Blank    | |

Example 2

Identification Assay of the Habitat of *Tribolium castaneum* Using Real-Time PCR (A) Insects The insects of *Tribolium castaneum* used in this example were those collected in the field of Saitama Prefecture (Urawa) (Urawa 2) and those found in flour exported from Canada to Hong Kong (Canada 4).

(B) DNA Extraction

DNA was extracted in the same manner as described in Example 1.

(C) Synthesis of TaqMan® MGB Probes

Based on the fact that the 229th nucleotide counted from the 5'-end of the COI gene is G in the insects from the main island of Japan in contrast to A in those from abroad areas, the following MGB probes were synthesized.

For insects from the main island of Japan (KN_CO1-C229V1; reporter dye VIC)

CAACCGGGATTAAAA    (SEQ ID NO: 30)

For insects from abroad areas (KN_CO1-C229M1; reporter dye FAM)

CAACCGGAATTAAAA.    (SEQ ID NO: 31)

The following primers for PCR were also synthesized.

KNCO1-C229F:
                                 (SEQ ID NO: 32)
AGCCTATTTCACTTCAGCCACAAT

KNCO1-C229R:
                                 (SEQ ID NO: 33)
ATGAATTTGCTAAGATTACTCCTGTTAGTCC

These are located as follows. That is, the primers are underlined and the MGB probes are double-underlined in the sequence below. The following sequence corresponds to an amplified fragment of 179 bp in length including the primer set.

TABLE 4

AGANGTNTACATTCTAATTCTNCCAGGATTTGGNATAATCTCCCACAT

TATTAGACAAGAAAGAGGAAAGAAAGAAGCATTTGGAACACTAGGAAT

AATTTATGCAATAATAGCAATTGGNCTCTTAGGTTTTGTTGTATGNGC

CCANCACATATTTACCGTAGGAATAGACGTTGATACTCGAGCCTATTT

CACTTCAGCCACAATAATTATTGCTGTNCCAACCGG[G/A]ATTAAAA

TTTTTAGATGACTAGC[T/C]ACTCTTCACGGCACTCAAATTAATTAT

AGNCCTTCTATAATATG[G/A]GCACTAGGATTTGTATTCNTATTTAC

AGTGGGNGGACTAACAGGAGTAATCTTAGCAAATTCATCAATTGANAT

TATACTT (SEQ ID NO: 36)

The design and synthesis of the probes and primers relied on Custom TaqMan® Gene Expression/SNP Genotyping Assays service of ABI.

(D) PCR

PCR was performed following the manual attached to the primers and probe prepared by Custom TaqMan® Gene Expression/SNP Genotyping Assays service (TaqMan MGB probes, FAM and VIC dye-labeled). That is, 12.5 µl of TaqMan Universal PCR Master Mix, 0.625 µl of 40× Assay-Mix, and 0.5 or 1 µl of the DNA samples dissolved in 20 µl alone or as a mixture were added, and the solutions were brought to a final volume of 25 µl with pure water. These preparation solutions were placed in MicroAmp Optical 8-Tube Strip (0.2 ml) to perform real-time PCR using 7500 Real-Time PCR System under predetermined conditions (95° C. for 10 minutes, (92° C. for 15 seconds and 60° C. for 1 minute)×40 cycles).

(E) Results

Figure 17:
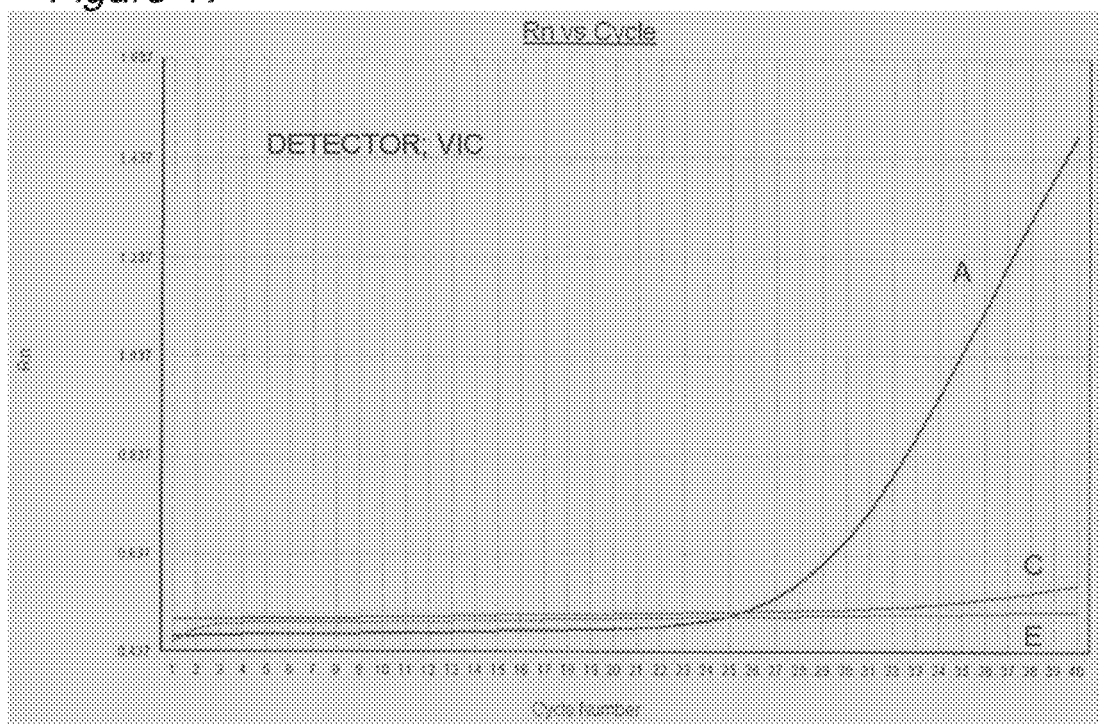
FIG. 17 is a diagram showing the results of detection of a fluorescent dye (VIC) used for labeling the probe for the main island of Japan in data analysis by real-time PCR.
Figure 18:
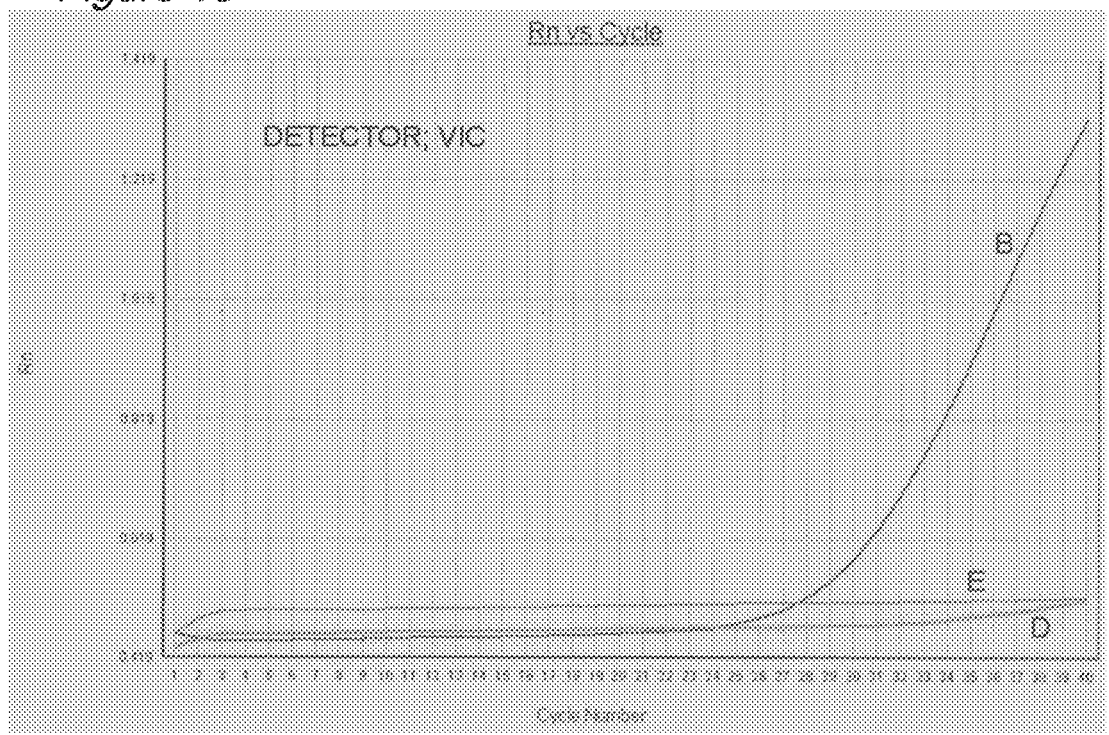
FIG. 18 is a diagram showing the results of detection of a fluorescent dye (VIC) used for labeling the probe for the main island of Japan in data analysis by real-time PCR.
Figure 19:
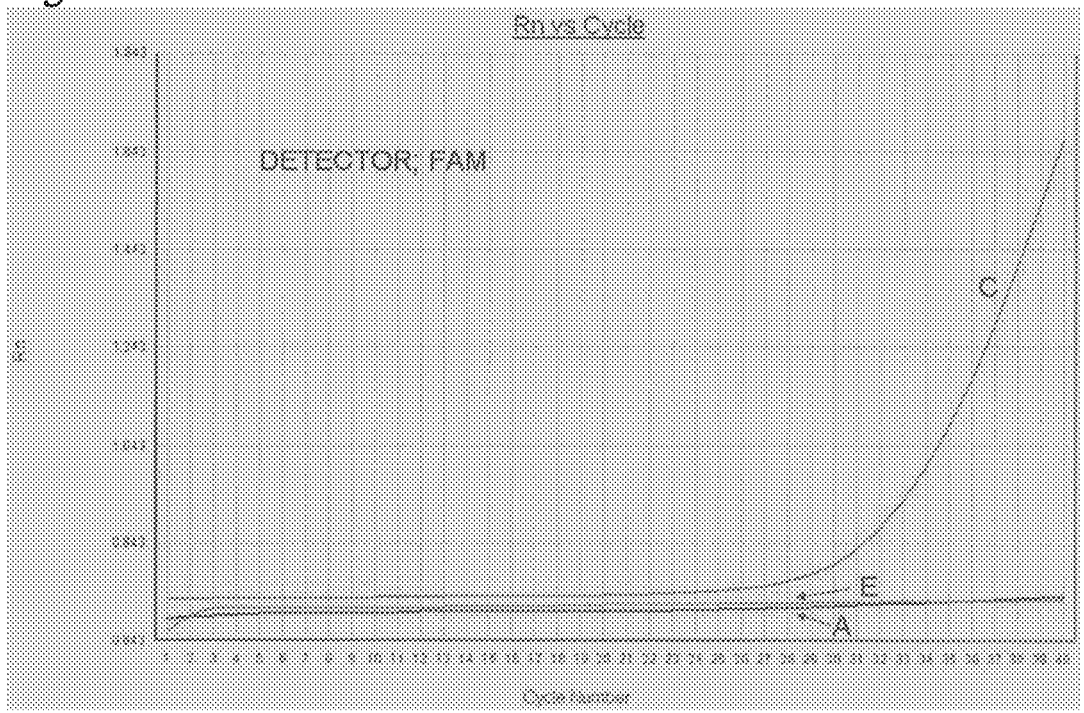
FIG. 19 is a diagram showing the results of detection of a fluorescent dye (FAM) used for labeling the probe for abroad areas in data analysis by real-time PCR.
Figure 20:
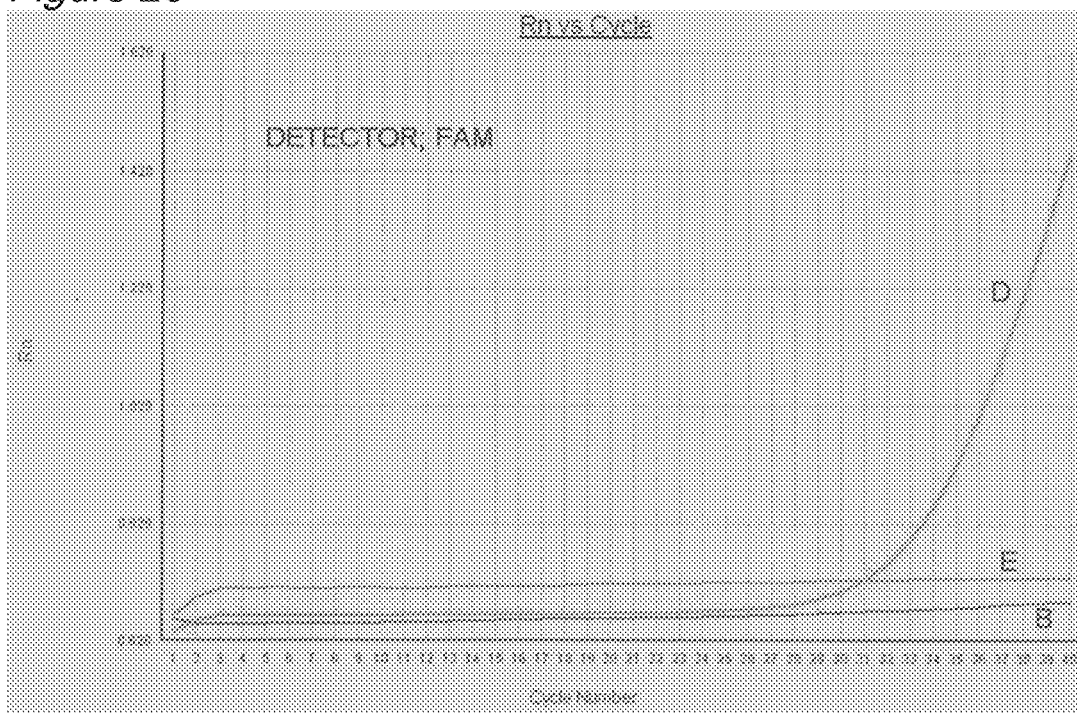
FIG. 20 is a diagram showing the results of detection of a fluorescent dye (FAM) used for labeling the probe for abroad areas in data analysis by real-time PCR.

FIGS. 17 and 18 show the results detected with the probe for the main island of Japan (VIC), revealing a rise indicative of amplification in DNA from Urawa 2 (A, B). However, no amplification was found in DNA from Canada 4 (C, D). Here, FIG. 17 shows data for 1 µl, wherein A is Urawa 2, C is Canada 4, and E is a blank. FIG. 18 shows data for 0.5 μl, wherein B is Urawa 2, D is Canada 4, and E is a blank. On the other hand, FIGS. 19 and 20 show the results detected with the probe for abroad areas (FAM), revealing a marked rise in Canada 4 (C, D). However, no PCR amplification was found in Urawa 2 (A, B). Here, FIG. 19 shows data for 1 μl, wherein A is Urawa 2, C is Canada 4, and E is a blank. FIG. 20 shows data for 0.5 μl, wherein B is Urawa 2, D is Canada 4, and E is a blank. Thus, the insects from the main island of Japan and others (from abroad areas) could be clearly discriminated.

Example 3

1. Sequence Data from Insects (A) Insects

The insects used for DNA extraction are the species of *Rhyzopertha dominica* belonging to the family Bostrychidae in the order Coleoptera, which is known as an insect of the same morphology inhabiting various areas of the world including Japan and ranks with *Sitophilus zeamais* as a very harmful insect damaging cereals of the family Gramineae such as rice and wheat. The insects of *Rhyzopertha dominica* used in this example were collected in Japan and China where they lived, and were individually raised.

(B) DNA Extraction to (H) Analysis of Nucleotide Sequences

The DNA of the COI region was extracted, amplified by PCR, and sequenced to provide sequence data by the same procedure as described in Example 1. The resulting sequence data are shown below.

1) COI Region (379 bp in Full Length)

Japan type 1 and China type 1 are shown below as SEQ ID NO: 34 and SEQ ID NO: 35, respectively.

Example 4

Evaluation of Amplification by PCR of DNA from Heat- or Pressure-Treated Samples Whether or not DNA of *Tribolium castaneum* artificially degraded by heat or pressure treatment can be amplified by PCR and whether or not its habitat can be identified by real-time PCR were evaluated.

(A) Insects

In this example, *Tribolium castaneum* purchased from Sumika Technoservice Corporation described in Example 1 (Takarazuka, Japan type 1) was used.

(B) Treatments of Samples

A. Two individuals of the insect were placed in 1 ml of Milli-Q water (in a microtube), which was boiled for 30 minutes or 60 minutes (using a microwave heater) and then rapidly cooled in ice.

B. A 100-ml tall beaker containing about 30 ml of Milli-Q water and two individuals of the insect was autoclaved at 121° C. for 15 min, then removed on the order of 50° C. and allowed to cool down naturally.

(C) DNA Extraction

DNA was extracted in the same manner as described in Example 1 (B).

(D) TaqMan® MGB Probes

Those described in Example 2 (C) were used.

(E) PCR

The following three methods were used.

A. PCR was performed in the same manner as described in Example 1 (C) with the primer set used for the analysis of the mitochondrial COI gene described in Example 1 (C) (L6625/H7005, amplified fragment size 435 bp).

B. PCR was performed using the primer set described in Example 2 (C) (KN_CO1-C229F/KN_CO1-C229R, ampli-

[Formula 15]

```
Japan    AGAAGTTTAC ATTTTAATCC TACCAGGATT TGGTATAATT TCTCATATTA TTAGACATGA AAGAGGAAAA AAGGAAACCT  80
China    AGAAGTTTAC ATTTTAATCC TACCAGGATT TGGTATAATT TCTCATATTA TTAGACATGA AAGAGGAAAA AAGGAAACCT  80
         ********** ********** ********** ********** ********** ********** ********** **********

Japan    TTGGTTCTCT AGCGATAATT TACGCAATAA TAGCAATTGG ACTATTAGGA TTTATTGTAT GAGCACATCA CATATTTACT  160
China    TTGGTTCTCT AGCGATAATT TACGCAATAA TAGCAATTGG ACTATTAGGA TTTATTGTAT GAGCACATCA CATATTTACC  160
         ********** ********** ********** ********** ********** ********** ********** *********

Japan    GTAGGAATAG ACGTAGATAC CCGAGCATAT TTTACTTCAG CAACAATAAT TATTGCAGTT CGAACCGGAA TTAAAGTATT  240
China    GTAGGAATAG ACGTAGATAC CCGAGCATAT TTTACTTCAG CAACAATAAT TATTGCAGTT CCAACCGGAA TTAAAGTATT  240
         ********** ********** ********** ********** ********** ********** ********** **********

Japan    TAGATGATTA GCTACCCTCC ACGGAACACA AATAAATTAT TCACCTTCAA TAATATGATC ATTAGGATTT GTCTTTCTAT  320
China    TAGATGATTA GCTACCGTCC ACGGAACAGA AATAAATTAT TCACCTTCAA TAATATGATC ATTAGGATTT GTCTTTCTAT  320
         ********** ****** *** ******** * ********** ********** ********** ********** **********

Japan    TTACCGTAGG AGGATTAACA GGAGTAGTAT TAGCAAATTC ATCCATTGAT ATTATTCTA                         379
China    TTACCGTAGG AGGATTAACA GGAGTAGTAT TAGCAAATTC ATCCATTGAT ATTATTCTA                         379
         ********** ********** ********** ********** ********** *********
```

In the sequences above, the sequence designated as "Japan" represents Japan type 1 of SEQ ID NO: 34 while the sequence designated as "China" represents China type 1 of SEQ ID NO: 35.

The above nucleotide sequences were analyzed by the same procedure as described in Example 1. As a result, a SNP (single nucleotide polymorphism) was found, i.e., the 160th nucleotide counted from the 5'-end of the resulting 379 nucleotides is "T" in Japan type 1 in contrast to "C" in China type 1.

fied fragment size 179 bp) in Veriti 96 Well Thermal Cycler from ABI under predetermined conditions (95° C. for 1 min, (92° C. for 15 sec+60° C. for 1 min)×40 cycles).

C. Real-time PCR was performed using the MGB probes in the same manner as described in Example 2.

(F) Results

Figure 25:
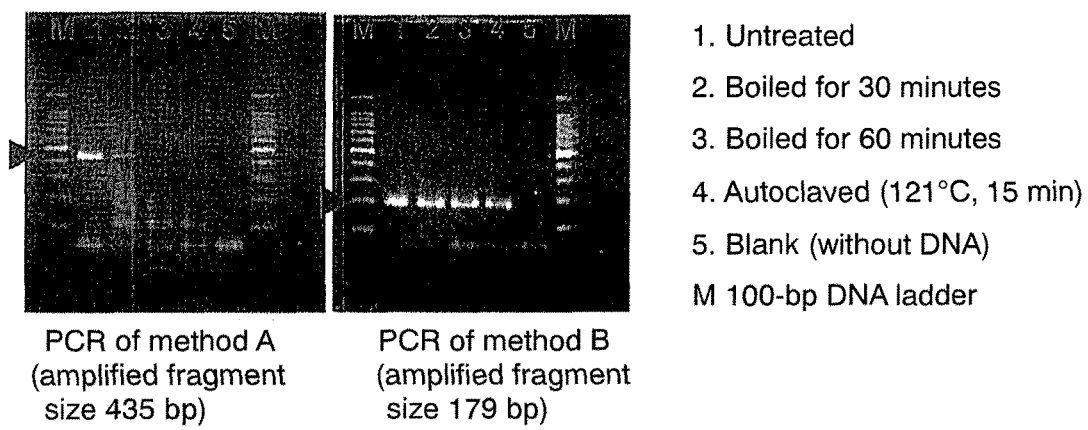
FIG. 25 is a photograph showing electrophoretic bands of DNA from *Tribolium castaneum* artificially degraded by heat or pressure treatment. Left panel shows the results of PCR of method A (amplified fragment size 435 bp), and right panel shows the result of PCR of method B (amplified fragment size 179 bp).

An amplified band of 435 bp allowing for a comparison of the entire set of criteria was found in the samples boiled for 30 minutes by method A above (FIG. 25, left panel, lane 2 indicated by an arrow, Table 5). However, this band was not found in the samples boiled for 60 min or autoclaved (121° C., 15 min) (FIG. 25, left panel, lanes 3, 4, Table 5). On the other hand, a 179-bp band allowing for the identification of Japan type 1 was found in the all cases by method B above (indicated by an arrow in FIG. 25, right panel, Table 5). Moreover, all the samples could be definitely identified as *Tribolium castaneum* of Japan type 1 (the main island of Japan) characteristic of these samples by real-time PCR using the MGB probes (method C above) (Table 6). Thus, it is difficult to identify the habitat of a sample insect by comparing the entire set of criteria when the DNA of the insect is fragmented, but even fragmented DNA can be assayed for habitat identification by selecting a nucleotide specific to one habitat and using primers and probes designed on the basis of the nucleotide.

TABLE 5

| Sample | Bath | Temperature | Period | Amplification by PCR | |
|---|---|---|---|---|---|
| | | | | 435 bp | 179 bp |
| Untreated | Pure water | 100° C. | 0 minute | Yes | Yes |
| Boiled for 30 minutes | Pure water | 100° C. | 30 minutes | Yes | Yes |
| Boiled for 60 minutes | Pure water | 100° C. | 60 minutes | No | Yes |
| Autoclaved | Pure water | 121° C. | 15 minutes | No | Yes |

TABLE 6

| Sample | Detector | | | Judgment |
|---|---|---|---|---|
| | Fluorescent dye | Discriminable type | Amplification by real-time PCR | |
| Untreated | VIC | Main island | Yes (29.3)** | Main island type |
| | FAM | Non-main island | No | |
| Boiled for 30 minutes | VIC | Main island | Yes (31.1) | Main island type |
| | FAM | Non-main island | No | |
| Boiled for 60 minutes | VIC | Main island | Yes (35.2) | Main island type |
| | FAM | Non-main island | No | |
| A/C* | VIC | Main island | Yes (37.2) | Main island type |
| | FAM | Non-main island | No | |
| Blank (without DNA) | VIC | Main island | No | |
| | FAM | Non-main island | No | |

*A/C: Autoclaved (121° C., 15 min)
**( ): Number of cycles for the first detection with the fluorescent dye Example 5

Evaluation of Amplification by PCR of DNA from Individuals Having Died of Natural Causes Whether or not DNA of *Tribolium castaneum* having died of natural causes can be amplified by PCR was evaluated.

(A) Insects

In this example, *Tribolium castaneum* (habitat unknown) stored at room temperature for 5 months after having died of natural causes during raising was used.

(B) DNA Extraction and PCR

DNA was extracted from two individuals of the insect in the same manner as described in Example 1 and subjected to PCR in the same manner as described in Example 4 (E) A.

(C) Results

Figure 26:
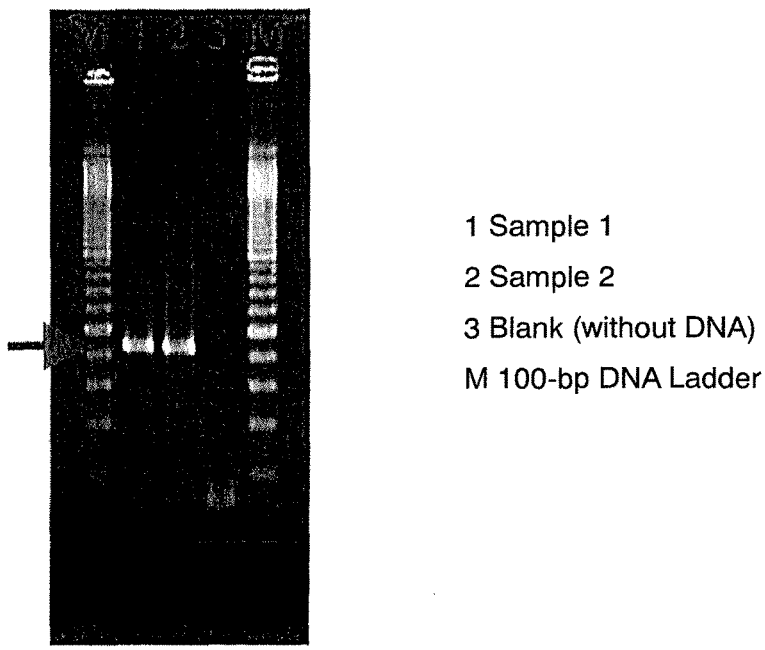
FIG. 26 is a photograph showing electrophoretic bands of DNA from *Tribolium castaneum* having died of natural causes.

An amplified band of 435 bp allowing for a comparison of the entire set of criteria was found in both individuals (indicated by an arrow in FIG. 26).

Example 6

Evaluation of Amplification by PCR of DNA from Samples Irradiated with Gamma Rays Whether or not DNA of *Tribolium castaneum* artificially degraded by gamma irradiation can be amplified by PCR and whether or not its habitat can be identified by real-time PCR were evaluated.

(A) Insects

In this example, *Tribolium castaneum* collected in a rice mill in Tsukuba-city was used (including Japan type 1 and non-Japan type 1).

(B) Treatments of Samples

Individuals of the insect (including Japan type 1 and non-Japan type 1) were irradiated with 60-Co gamma rays using a gamma irradiator (Gamma Cell 220 from Nordion) to prepare samples. The doses (Gy) were set at two levels of 1.5 K and 2 K for irradiation periods of 810 seconds and 18 minutes, respectively. The accurate doses under this irradiation condition were determined from a calibration curve prepared using an alanine dosimeter (Alanine Pellet Dosimeter ES200-2106, Bruker Biospin) were 1623 and 2142 Gy, respectively.

(C) DNA Extraction and PCR

Figure 27:
FIG. 27 is a photograph showing electrophoretic bands of DNA from *Tribolium castaneum* artificially degraded by gamma irradiation.

DNA was extracted in the same manner as in Example 1 from the samples damaged under the conditions of the preset levels of 1.5 KGy and 2 KGy as described above (two samples were tested under each condition; designated as 1.5K-1, 1.5K-2, 2K-1 and 2K-2 in FIG. 27 and Table 7, respectively) and amplified by PCR in the same manner as described in Example 4 (E) A and C.

(D) Results

When DNA was extracted from the four test samples (1.5K-1, 1.5K-2, 2K-1 and 2K-2, respectively) and used as a template for normal PCR (method described in Example 4 (E) A), the desired amplified band of 435 bp in size was not found in three samples of the four samples excluding one irradiated with 2 KGy, suggesting that DNA fragmentation has proceeded (indicated by an arrow in FIG. 27). When the same template DNA was subjected to real-time PCR (method described in Example 4 (E) C) using the MGB probes, a PCR reaction was observed in all of the four samples and even definite habitat identification could be achieved, i.e., 2K-1, 2K-2 and 1.5K-2 were identified as main island type and only 1.5K-1 was identified as non-main island type (Table 7).

TABLE 7

| Sample | Detector | | | Judgment |
|---|---|---|---|---|
| | Fluorescent dye | Discriminable type | Amplification by real-time PCR | |
| 2K-1 | VIC | Main island | Yes (32.6)* | Main island type |
| | FAM | Non-main island | No | |
| 2K-2 | VIC | Main island | Yes (32.7) | Main island type |
| | FAM | Non-main island | No | |
| 1.5K-1 | VIC | Main island | No | Non-main island type |
| | FAM | Non-main island | Yes (32.4) | |
| 1.5K-2 | VIC | Main island | Yes (33.0) | Main island type |
| | FAM | Non-main island | No | |
| Blank (without DNA) | VIC | Main island | No | |
| | FAM | Non-main island | No | |

*( ): Number of cycles for the first detection with the fluorescent dye

SEQUENCE LISTING FREE TEXT

SEQ ID NO: 13: primer
SEQ ID NO: 14: primer
SEQ ID NO: 15: primer
SEQ ID NO: 16: primer
SEQ ID NO: 17: primer
SEQ ID NO: 18: primer
SEQ ID NO: 19: primer
SEQ ID NO: 20: primer
SEQ ID NO: 21: primer
SEQ ID NO: 22: primer
SEQ ID NO: 23: primer
SEQ ID NO: 24: primer
SEQ ID NO: 25: primer
SEQ ID NO: 26: primer
SEQ ID NO: 27: primer
SEQ ID NO: 28: primer
SEQ ID NO: 29: primer
SEQ ID NO: 30: probe
SEQ ID NO: 31: probe
SEQ ID NO: 32: primer
SEQ ID NO: 33: primer

The invention claimed is:

1. A method for preparing a criterion for identifying a *Tribolium castaneum* habitat or *Rhyzopertha dominica* habitat, comprising the steps of:
 (a) obtaining, by a processor, the nucleotide sequences of a region of mitochondrial DNA of one or more *Tribolium castaneum* or *Rhyzopertha dominica* from two or more habitats, wherein the region of mitochondrial DNA comprises at least one of a cytochrome oxidase subunit I (COI) gene and a NADH dehydrogenase subunit 5 (ND5) gene, and wherein the nucleotide sequences are amplified using a primer pair comprising SEQ ID NOs: 13 and 14 for COI, and/or SEQ ID NOs: 15 and 16 for ND5;
 (b) aligning the nucleotide sequences determined in said step (a);
 (c) eliminating sites consisting of one or more nucleotides conserved in all of the nucleotide sequences aligned in said step (b) from the nucleotide sequences;
 (d) defining all or a part of the sites remaining upon elimination in said step (c) as type-discriminating sites, wherein a type discriminating site is amplified by a primer selected from the group consisting of SEQ ID NOs: 17-29;
 (e) comparing, by the processor, nucleotides corresponding to each other in the type-discriminating sites obtained in said step (d) to classify completely identical type-discriminating sites as the same type and incompletely identical type-discriminating sites as one or more different types; and
 (f) determining the habitat of each type classified in said step (e) on the basis of *Tribolium castaneum* or *Rhyzopertha dominica* habitats belonging to each type, thereby defining the type-discriminating site of each type as a criterion, wherein one or more criteria are selected from the group consisting of:
  (i) the 229th nucleotide from the 5'-end of the nucleotide sequence corresponding to the *Tribolium castaneum* COI gene of SEQ ID NO: 1 is G, the 253rd nucleotide is T, and the 298th nucleotide is G;
  (ii) the 248th nucleotide from the 5'-end of the nucleotide sequence corresponding to the *Tribolium castaneum* ND5 gene of SEQ ID NO: 8 is A; and
  (iii) the 160th nucleotide from the 5'-end of the nucleotide sequence corresponding to *Rhyzopertha dominica* COI gene of SEQ ID NO: 34 is T.

2. The method of claim 1, further comprising the steps of:
 (g) comparing nucleotides corresponding to each other in the criteria obtained in step (f) as defined in claim 1 to extract one or more nucleotides existing in only one type but not in the other types; and
 (h) defining the one or more nucleotides extracted in said step (g) alone or in combination, as an area-discriminating criterion that identifies whether the habitat of *Tribolium castaneum* or *Rhyzopertha dominica* is the same.

* * * * *